US012414923B2

(12) United States Patent
Callan et al.

(10) Patent No.: US 12,414,923 B2
(45) Date of Patent: Sep. 16, 2025

(54) SONODYNAMIC THERAPY

(71) Applicant: INNOVATION ULSTER LIMITED, Antrim (GB)

(72) Inventors: John Callan, Antrim (GB); Anthony Mchale, Antrim (GB); Sian Farrell, Antrim (GB)

(73) Assignee: INNOVATION ULSTER LIMITED, Antrim (GB)

( * ) Notice: Subject to any disclaimer, the term of this patent is extended or adjusted under 35 U.S.C. 154(b) by 815 days.

(21) Appl. No.: 17/624,430

(22) PCT Filed: Jul. 2, 2020

(86) PCT No.: PCT/GB2020/051587
§ 371 (c)(1),
(2) Date: Jan. 3, 2022

(87) PCT Pub. No.: WO2021/005337
PCT Pub. Date: Jan. 14, 2021

(65) Prior Publication Data
US 2023/0095572 A1 Mar. 30, 2023

(30) Foreign Application Priority Data
Jul. 5, 2019 (GB) ..................................... 1909692

(51) Int. Cl.
*A61K 49/00* (2006.01)
*A61K 9/51* (2006.01)
*A61K 31/352* (2006.01)
*A61K 31/403* (2006.01)
*A61K 31/4745* (2006.01)
*A61K 41/00* (2020.01)
*A61P 1/18* (2006.01)
*A61P 35/00* (2006.01)
*A61P 35/04* (2006.01)

(52) U.S. Cl.
CPC .......... *A61K 9/5146* (2013.01); *A61K 9/5153* (2013.01); *A61K 31/352* (2013.01); *A61K 31/403* (2013.01); *A61K 31/4745* (2013.01); *A61K 41/0033* (2013.01); *A61K 49/0054* (2013.01); *A61P 1/18* (2018.01); *A61P 35/00* (2018.01); *A61P 35/04* (2018.01)

(58) Field of Classification Search
None
See application file for complete search history.

(56) References Cited

U.S. PATENT DOCUMENTS

| 11,382,987 | B2 * | 7/2022 | Callan | ................. | A61K 47/6925 |
| 11,878,059 | B2 * | 1/2024 | Callan | ................. | A61K 41/0033 |
| 2011/0020225 | A1 | 1/2011 | Chung et al. | | |

FOREIGN PATENT DOCUMENTS

| CN | 105194670 | 12/2015 |
| WO | 98/52609 | 11/1998 |

OTHER PUBLICATIONS

Nomikou, N. et al., "A versatile, stimulus-responsive nanoparticle-based platform for use in both sonodynamic and photodynamic cancer therapy," Acta Biomaterialia, Vo. 49, pp. 414-421 (2017).*
International Search Report and Written Opinion issued Oct. 8, 2020 in International (PCT) Application No. PCT/GB2020/051587.
Jian, Wei-Hong et al., "Indocyanine Green-Encapsulated Hybrid Polymeric Nanomicelles for Photothermal Cancer Therapy", Langmuir, vol. 31, No. 22, 2015, pp. 6202-6210.
Loya-Castro, Maria F. et al., "Preparation of PLGA/Rose Bengal colloidal particles by double emulsion and layer-by-layer for breast cancer treatment", Journal of Colloid and Interface Science, 2018, vol. 518, pp. 122-129.
Adeli, M. et al., "Effect of the shell on the transport properties of poly(glycerol) and Poly(ethylene imine) nanoparticles", Journal of Nanoparticle Research, 2007, vol. 9, No. 6, pp. 1057-1065.
Adeli, M. et al., "Multiarm Star Nanocarriers Containing a Poly-(ethylene imine) Core and Polylactide Arms", Journal of Polymer Science, Part A: Polymer Chemistry, 2006, vol. 44, pp. 5740-5749.
Yue, Wenwen et al., "Checkpoint blockade and nanosonosensitizer-augmented noninvasive sonodynamic therapy combination reduces tumour growth and metastases in mice", Nature Communications, 2019, vol. 10, No. 1, 15 pages.
Tsuru, Hirofumi et al., "Tumor growth inhibition by sonodynamic therapy using a novel sonosensitizer", Free Radical Biology and Medicine, 2012, vol. 53, No. 3, pp. 464-472.
Mcewan, Conor et al., "Combined sonodynamic and antimetabolite therapy for the improved treatment of pancreatic cancer using oxygen loaded microbubbles as a delivery vehicle", Biomaterials, 2016, vol. 80, pp. 20-32.
Zhang, Q. et al.. "Sonodynamic therapy-assisted immunotherapy: A novel modality for cancer treatment", Cancer Science, 2018, vol. 109, pp. 1330-1345.
Mcewan, Conor et al., "Polymeric Microbubbles as Delivery Vehicles for Sensitizers in Sonodynamic Therapy", Langmuir, 2014, vol. 30, pp. 14926-14930.
Sun, Danyang et al., "Clinical observation of immune checkpoint inhibitors in the treatment of advanced pancreatic cancer: a real-world study in Chinese cohort", Therapeutics and Clinical Risk Management, 2018, vol. 14, pp. 1691-1700.
Morrison, Alexander H. et al., "Immunotherapy and prevention of pancreatic cancer", Trends Cancer., 2018, vol. 4, No. 6, pp. 418-428.

(Continued)

*Primary Examiner* — John Pak
(74) *Attorney, Agent, or Firm* — Wenderoth, Lind & Ponack, L.L.P.

(57) ABSTRACT

The invention provides polymeric particles comprising a matrix of a biocompatible polymer and polyethylene imine, said matrix having incorporated therein an anionic or hydrophobic sonosensitiser and, optionally, an immunomodulatory agent and/or an imaging agent. Such particles find use in methods of sonodynamic therapy, in particular in methods of combined sonodynamic therapy and immunotherapy, for example in the treatment of cancer, metastasis or micrometastasis derived from cancer. The invention is particularly suitable for the treatment of deep-sited, hard to treat tumours such as pancreatic cancer.

19 Claims, 9 Drawing Sheets

(56) References Cited

OTHER PUBLICATIONS

International Preliminary Report on Patentability and Written Opinion of the International Searching Authority issued Jan. 11, 2022 in International (PCT) Application No. PCT/GB2020/051587.

* cited by examiner

SONODYNAMIC THERAPY

TECHNICAL FIELD

The present invention relates to polymeric particles having a sonosensitiser incorporated therein and to methods for their preparation. It further relates to the use of such particles in methods of sonodynamic therapy and, in particular, in the sonodynamic treatment of deeply-sited tumours (e.g. pancreatic cancer) and their associated metastases.

More specifically, the invention relates to methods of sonodynamic therapy in which polymeric particles having a sonosensitiser incorporated therein deliver a sonodynamic-induced abscopal effect which modulates a systemic regression of metastatic disease, and which can additionally deliver a protective effect against the subsequent formation of disease. These effects may be further enhanced by the incorporation of an immunomodulatory agent (e.g. imiquimod) in the particles.

Incorporation of an imaging agent in the polymeric particles enables these to simultaneously provide an imaging capability (e.g. a near infra-red imaging capability) that can be employed to monitor the uptake of the particles prior to sonodynamic treatment.

BACKGROUND OF THE INVENTION

Conventional treatment of deeply-sited tumours typically involves major surgery, chemotherapy, radiotherapy or combinations of all of these. All three interventions may result in various complications including sepsis. Therefore, the development of more targeted and less invasive therapeutic approaches with improved efficacy to treat such patients is highly sought after. Pancreatic cancer is one example of a deeply-sited tumour. It remains one of the most lethal types of cancer known with less than 20% of those diagnosed being eligible for curative surgical treatment. It accounts for approximately 2% of all cancers with a five year survival of 15-21% in patients who have a surgical resection followed by systemic chemotherapy.

Methods known for use in the treatment of cancer include photodynamic therapy (PDT). PDT involves the application of photosensitizing agents to the affected area, followed by exposure to photoactivating light to convert these into cytotoxic form. This results in the destruction of cells and surrounding vasculature in a target tissue. Photosensitisers which are currently approved for use in PDT absorb light in the visible region (below 700 nm). However, light of this wavelength has limited ability to penetrate the skin; this penetrates to a surface depth of only a few mm. Whilst PDT may be used to treat deeper sited target cells, this generally involves the use of a device, such as a catheter-directed fibre optic, for activation of the photosensitizer. Not only is this a complicated procedure, but it precludes access to certain areas of the body. It also compromises the non-invasive nature of the treatment. Thus, although appropriate for treating superficial tumours, the use of PDT in treating deeply seated cells, such as tumour masses, and anatomically less accessible lesions is limited.

Sonodynamic therapy (SDT) represents a targeted approach to the treatment of solid tumours. It involves the administration of a harmless sonosensitiser (also referred to herein as a "sonosensitising agent") that, upon exposure to ultrasound, results in the generation of cytotoxic reactive oxygen species (ROS) at the exposure site (tumour). Such species are cytotoxic, thereby killing the target cells or at least diminishing their proliferative potential. Since ultrasound readily propagates through several cm of tissue, SDT provides a means by which tumours which are located deep within tissues may be treated. Ultrasound energy can also be focused on a tumour mass in order to activate the sonosensitiser thereby restricting its effects to the target site.

Many cancers still remain largely incurable. At least in part this is due to a step change from localised to metastatic disease in which cancer cells spread throughout the body. Tumours have also evolved to evade the body's own immune system. Immunotherapy represents an exciting development in the treatment of cancer and involves stimulating or priming a patient's immune system to seek out and destroy cancer cells. One class of immunotherapy is the use of immune checkpoint inhibitors which have been shown to be effective in treating certain cancers such as melanoma and lung cancer. However, their effect in pancreatic cancer is poor. In clinical trials, immune checkpoint blockade has shown little benefit in the treatment of pancreatic ductal adenocarcinoma (PDAC) (see Morrison et al., Trends in Cancer (2018) 4:418-428), for example. Two main reasons have been suggested for the poor effect of immune checkpoint inhibitors in pancreatic cancer: (i) pancreatic tumours are characterised by a highly immunosuppressive tumour microenvironment meaning that a low amount of cancer-fighting immune cells are produced; and (ii) pancreatic tumours have a dense protective coating called a "stroma" that acts as a barrier to entry for the cancer-fighting immune cells.

Any therapy that results in cell death, such as chemotherapy, radiotherapy, PDT, or SDT, also has the potential to generate immunogenic damage associated molecular patterns (DAMPs) that essentially result from disintegrating cells. It has been suggested that this is the reason for the observed abscopal effects during radiotherapy and PDT, in which a localised chemotherapeutic treatment of the primary lesion stimulates the immune system and modulates the systemic regression of distant (e.g. metastatic) cancers. Such responses can be triggered more effectively when combining the cancer treatment (e.g. radiotherapy) with immunotherapy. The effect of SDT using HPD (HiPorfin, a hematoporphyrin derivative) on the induction of a systemic immune response has been investigated in liver cancer cell lines (see Zhang et al., Cancer Science 2018:109:1330-1345). In this report, the authors describe the use of HPD together with ultrasound to facilitate SDT and demonstrate an immunosuppressive abscopal effect. However, relatively little is still known about the abscopal response in SDT, particularly in the context of treating pancreatic tumours.

More recently, Yue et al. (Nature Communications 2019: 10 (1): 2025) have described a liposomal formulation containing hematoporphyrin monomethyl ether (HMME) as a sonosensitiser and imiquimod (R837, a TLR7 agonist) as an immunomodulator. Together with an anti-PD-L1 immune checkpoint inhibitor, the authors demonstrate an abscopal effect in breast cancer and colorectal cancer murine models and demonstrate protective immune memory when the animals were re-challenged with cancer.

It cannot be predicted whether the abscopal effects seen in these earlier tumour models would extend to other tumours, especially to pancreatic tumours due to the challenges associated with its treatment, for example as evidenced by the well-recognised ability of its stroma to protect the cancer cells from attack by the immune system and the current failure of existing immunotherapy in treating pancreatic cancer (see, for example, Sun et al., Ther. Clin. Risk Manag. (2018) 14:1691-1700). Furthermore, the generation of "synergy" between any chemotherapy treatment and immunotherapy required to provide local treatment of tumours and induce an abscopal effect is inherently unpredictable due to the many different factors affecting the tumour immune interaction, e.g. chemotherapy-induced immunosuppression.

There is a continuing need for alternative (e.g. improved) methods for the treatment of deeply-sited, inaccessible tumours and metastases derived therefrom. In particular, a need still exists for such methods for the treatment of pancreatic cancer and its metastases.

SUMMARY OF THE INVENTION

Biocompatible and biodegradable polymer materials are widely known for use in the medical field, for example as surgical sutures, as scaffold materials for inducing tissue regeneration, as carriers for the delivery of drugs and genes, etc. Amongst such materials are copolymers of lactic and glycolic acids (PLGA). These have been studied extensively and commercialised due to their excellent biocompatibility and ability to degrade in vivo into harmless substances.

The use of polymeric particles in the transport of drugs and genes in vivo is well known. For example, Castro et al. (Journal of Colloid and Interface Science 518 (2018): 122-129) describe the use of PLGA colloidal particles containing Rose Bengal (RB) for the purpose of non-stimulus responsive toxicity in breast cancer treatment. The authors recognise the low stability of the PLGA/RB colloidal particles and suggest this may be addressed using known methods such as coating of the particles with stabilising agents such as poly(ethylene glycol) (PEG), or charged polymers such as chitosan, or poly(ethylene imine) (PEI).

The inventors now propose that polymeric particles, such as PLGA, may be used to entrap and deliver a sonosensitiser for use in SDT by a suitable modification of the polymeric matrix of the particle. Specifically, they propose the entrapment of an anionic or hydrophobic sonosensitiser inside a polymeric particle which comprises a matrix of a biocompatible polymer, such as poly(D,L-lactic-co-glycolic acid) (PLGA), and polyethylene imine (PEI).

By incorporating PEI into the particle, the inventors have found that an anionic or hydrophobic sonosensitiser can be effectively loaded to the inside of the particles and delivered to target tissues in vivo. The inventors also propose that such particles may additionally entrap an immunomodulatory agent, such as imiquimod. Using a pancreatic cancer model, the inventors have demonstrated that these particles can deliver an abscopal effect which is greater than that delivered by SDT at the target tumour, and that they can additionally deliver a protective effect against the subsequent formation of disease. The incorporation of an imaging agent (e.g. a NIR imaging agent or contrast agent) into the particles further enables these to provide an imaging capability that can be employed to monitor their uptake prior to sonodynamic treatment.

In view of these findings, the inventors propose various improvements in and relating to SDT in which polymeric particles are employed as a carrier for an anionic or hydrophobic sonosensitiser.

Specifically, the inventors propose that such therapy may be used not only in the targeted treatment of a primary tumour, but in view of the potential of this treatment to initiate an "abscopal" effect, they propose its extended use in the treatment of non-targeted tumours, e.g. in the treatment of metastatic disease or circulating tumour cells (CTCs), and in the treatment of other non-targeted primary tumours. The inventors' findings also offer the potential of additive effects, or even synergy, of particle-delivered SDT in combination with an immunotherapy-based strategy and so they now propose the treatment of tumours (both primary and metastatic tumours) using polymeric particles to deliver SDT in combination with an immunomodulatory agent, such as imiquimod. Their findings relating to the development of a protective immune memory when animals were re-challenged with cancer further extends to the use of the polymeric particles herein described to provide a protective (i.e. prophylactic) effect against the development of secondary lesions.

These proposals are considered to be of particular benefit in the context of treating pancreatic cancer. In particular, these provide a minimally invasive and highly focused treatment with the ability to significantly reduce tumour burden in pancreatic cancer. These are also expected to provide significant benefits in terms of improved survival rates for patients with pancreatic cancer and a better quality of life during treatment (due to the reduction in side-effects of SDT when compared to current standard of care drug-based treatments). While the detailed disclosure provided herein is focused on the treatment of pancreatic cancer, this is not intended to be limiting. Any of the polymeric particles, products, formulations, compositions, methods, uses and kits herein described are considered to be suitable for the treatment of other cancers, in particular other deeply-sited cancers and metastatic diseases.

In one aspect the invention provides a polymeric particle comprising a matrix of a biocompatible polymer and polyethylene imine (PEI), said matrix having incorporated therein an anionic or hydrophobic sonosensitiser and, optionally, an immunomodulatory agent and/or an imaging agent.

In another aspect the invention provides a particulate composition comprising a plurality of polymeric particles as herein described.

In another aspect the invention provides a polymeric particle or particulate composition as herein described for use in therapy or for use as a medicament, preferably for use in a method of sonodynamic therapy, e.g. for use in a method of combined sonodynamic therapy and immunotherapy.

In another aspect the invention provides a pharmaceutical composition comprising a polymeric particle as herein described, together with at least one pharmaceutical carrier or excipient. In another aspect, the invention provides such a composition for use in therapy or for use as a medicament, for example for use in a method of sonodynamic therapy.

In another aspect the invention provides a polymeric particle or particulate composition as herein described for use in the manufacture of a medicament for use in a method of sonodynamic therapy, e.g. for use in a method of combined sonodynamic therapy and immunotherapy.

In another aspect the invention provides a method of sonodynamic therapy, e.g. a method of combined sonodynamic therapy and immunotherapy, said method comprising the step of administering to cells or tissues of a subject in need thereof (e.g. a patient) a pharmaceutically effective amount of a polymeric particle or particulate composition as herein described, or a pharmaceutical composition comprising a polymeric particle as herein described, and subjecting said cells or tissues to ultrasound irradiation.

In another aspect the invention provides a polymeric particle or particulate composition as herein described for use in a method of sonodynamic therapy comprising simultaneous, separate or sequential use of an immune checkpoint inhibitor.

In another aspect the invention provides a method of sonodynamic therapy which comprises at least the following steps:

(a) administering a polymeric particle or particulate composition as herein described to affected cells or tissues of a subject in need thereof (e.g. a patient) and subjecting said cells or tissues to ultrasound irradiation; and (b) simultaneously, separately or sequentially administering to said subject (e.g. said patient) a pharmaceutically effective amount of an immune checkpoint inhibitor.

In another aspect the invention provides a product comprising a polymeric particle or particulate composition as herein described and an immune checkpoint inhibitor for simultaneous, separate or sequential use in a method of sonodynamic therapy.

In another aspect the invention provides a kit (or pharmaceutical pack) comprising the following components: (i) a polymeric particle or particulate composition as herein described; and separately (ii) an immune checkpoint inhibitor; optionally together with (iii) instructions for the use of said components in a method of sonodynamic therapy.

DETAILED DESCRIPTION OF THE INVENTION

Definitions

As used herein, the term "polymeric particle" refers to a particle which comprises one or more polymers and which may be approximately spherical or have other geometries. A "polymeric particle" may have a polymeric core or it may have a polymeric shell. A particle having a polymeric core may be approximately homogenous in composition. These particles are generally referred to herein as "spheres", though these need not be spherical in shape. A particle having a polymeric shell will comprise a core having a composition which is distinct from its surrounding shell. The core of the particle may be hollow, for example it may comprise a gas. Particles having a polymeric shell are generally referred to herein as "capsules". These need not be spherical in shape.

As used herein the term "microparticle" refers to a particle having at least one dimension (e.g. a diameter) which is less than about 1 mm. Microparticles include both microspheres and microcapsules.

As used herein the term "nanoparticle" refers to a particle having at least one dimension (e.g. a diameter) which is less than about 1 μm. Nanoparticles include both nanospheres and nanocapsules.

It will be understood that the terms "particle", "microparticle" and "nanoparticle" as used herein do not imply any particular shape, but include all known shapes including, but not limited to, a sphere, a rod, and any other substantially spherical shape such as an ovoid.

The term "biocompatible" refers to a material that does not typically induce an adverse response when inserted or injected into a living subject, for example, it does not result in significant inflammation and/or acute rejection of the material by the immune system, e.g. via a T-cell-mediated response.

The term "biodegradable" refers to a material that degrades either chemically and/or biologically within a physiological environment, such as within a body tissue (e.g. ex vivo) or within the body of a living subject, over time, specifically within a period of time that is acceptable in the given therapeutic situation. Biodegradation may occur after exposure to physiological pH and temperature, e.g. a pH ranging from 6 to 8 and a temperature ranging from 25 to 37° C.

The terms "sonosensitiser" and "sonosensitising agent" are used interchangeably herein and are intended to refer to any compound which is capable of converting acoustic energy (e.g. ultrasound) into reactive oxygen species (ROS), such as singlet oxygen, that results in cell toxicity.

As used herein, the terms "sonodynamic therapy" and "sonodynamic treatment" are intended to refer to a method involving the combination of ultrasound and a sonosensitiser in which activation of the sonosensitiser by acoustic energy results in the generation of reactive oxygen species, such as singlet oxygen.

As used herein, the term "immunomodulatory agent" refers to an agent that modulates an immune response in a living subject. "Modulate", as used herein, refers to inducing, enhancing, stimulating, or directing an immune response. Such agents may affect specific parts of the immune system, or they may have non-specific activity and affect the immune system generally. Examples of such agents include immunostimulatory agents that stimulate (or boost) an immune response to an antigen. Non-limiting examples of immunomodulatory agents are listed herein and include, for example, immunoadjuvants and immune checkpoint inhibitors.

Immune checkpoints are known in the art and the term is well understood in the context of cancer therapy. Perhaps the most well-known are PD-1 and its ligand PDL-1, and CTLA-4. Others include OX40, TIM-3, KIR, LAG-3, VISTA and BTLA. Inhibitors of immune checkpoints, herein referred to as "immune checkpoint inhibitors", inhibit their normal immunosuppressive function, for example by down regulation of expression of the checkpoint molecules or by binding thereto and blocking normal receptor/ligand interactions. As the immune checkpoints put the brakes on the immune system response to an antigen, so an inhibitor thereof (i.e. an "immune checkpoint inhibitor") reduces this immunosuppressive effect and enhances the immune response.

As used herein, the term "cancer" refers to cells undergoing abnormal proliferation. Growth of such cells typically causes the formation of a tumour. Cancerous cells may be benign, pre-malignant or malignant. Such cells may be invasive and/or have the ability to metastasize to other locations in the body. The term cancer, as used herein, includes cancerous growths, tumours, and their metastases.

The term "tumour", as used herein, refers to an abnormal mass of tissue containing cancerous cells.

As used herein, the term "metastasis" refers to the spread of malignant tumour cells from one organ or part of the body to another non-adjacent organ or part of the body. Cancer cells may break away from a primary tumour, enter the lymphatic and blood systems and circulate to other parts of the body (e.g. to normal tissues). Here they may settle and grow within the normal tissues. When tumour cells metastasize, the new tumours may be referred to as a "secondary" or metastatic cancer or tumour. The term "metastatic disease" as referred to herein relates to any disease associated with metastasis.

As used herein, the term "micrometastasis" refers to a collection of cancer cells (also known as micrometastases or "micromets") which are shed from a primary tumour and which spread to another part of the body. The term "micrometastatic disease" is used herein in respect of any disease associated with micrometastasis.

The term "circulating tumour cells" (CTCs) refers to cells that are shed into the vasculature or lymphatics from a primary tumour and are carried around the body in the blood. CTCs act as seeds for the subsequent growth of additional tumours (metastases) in other organs or parts of the body.

The term "abscopal effect" refers to a phenomenon in the treatment of metastatic cancer in which localised treatment of a tumour causes not only a reduction in the volume of the treated tumour, but also shrinkage of tumours outside of the treated area.

As used herein, "treatment" includes any therapeutic application that can benefit a human or non-human animal (e.g. a non-human mammal). Both human and veterinary treatments are within the scope of the present invention, although primarily the invention is aimed at the treatment of humans. Treatment is intended to refer to the reduction, alleviation or elimination, of a disease, condition or disorder. It includes palliative treatment, i.e. treatment intended to minimise, or partially or completely inhibit the development of the disease, condition or disorder. Where not explicitly stated, treatment also encompasses prevention. As used herein, "prevention" refers to absolute prevention, i.e. maintenance of normal levels with reference to the extent or appearance of a particular symptom of the disease, condition or disorder, or to reduction or alleviation of the extent or timing (e.g. delaying) of the onset of that symptom.

By "a pharmaceutical composition" is meant a composition in any form suitable to be used for a medical purpose.

As used herein, a "pharmaceutically effective amount" relates to an amount that will lead to the desired pharmacological and/or therapeutic effect, i.e. an amount of the agent which is effective to achieve its intended purpose. While individual subject (e.g. patient) needs may vary, determination of optimal ranges for effective amounts of the active agent(s) herein described is within the capability of one skilled in the art. Generally, the dosage regimen for treating a disease, condition or disorder with any of the agents described herein may be selected by those skilled in the art in accordance with a variety of factors including the nature of the condition and its severity.

The term "subject" refers to any individual who is the target of the administration or treatment. The subject may be, for example, a mammal. Thus the subject may be a human or non-human animal. The term "patient" refers to a subject under the treatment of a clinician. Preferably, the subject will be a human.

The polymeric particles in accordance with the invention comprise a polymeric matrix, i.e. an entangled polymeric network, of a biocompatible polymer and polyethylene imine (PEI) in which the sonosensitiser is entrapped. In addition to the sonosensitiser, an immunomodulatory agent and/or an imaging agent may also be entrapped within the polymeric matrix. As noted herein, the polymeric particles need not necessarily be spherical in shape, although generally they will be approximately spherical.

The polymeric matrix may comprise the core or body of the particle (i.e. it extends throughout the structure of the particle) or it may comprise the particle shell. As will be understood, where the core of the particle is composed of the defined polymeric matrix, the particle will be generally homogenous in composition with the agent(s) being embedded throughout the particle. In the case where only the shell of the particle is composed of the defined polymeric matrix, the particle will be non-homogenous in composition with the active(s) being embedded in the shell and/or in the particle core.

Biocompatible polymers suitable for use in the invention include polymers known and described for use in the medical field and derivatives thereof. Mixtures (e.g. blends) of such polymers may also be used. Examples of suitable derivatives are biocompatible polymer materials which are linked to one or more hydrophilic polymers. Suitable hydrophilic polymers include poly(ethylene glycol) (PEG), poly (propylene glycol) (PPG) and copolymers of poly(ethylene glycol) and poly(propylene glycol). Other derivatives include those in which the polymer is linked to a targeting moiety, for example a moiety which enables targeting of the polymeric particle to tumour cells. For example, the polymer may be functionalised with folate to enable targeting to folate receptors on tumour cells.

The biocompatible polymer may, for example, be selected from the group consisting of poly(caprolactone) (PCL), poly(lactic acid) (PLA), poly(L-lactic acid) (PLLA), poly (glycolic acid) (PGA), poly(lactic acid-co-glycolic acid) (PLGA), poly(L-lactic acid-co-glycolic acid) (PLLGA), poly(D,L-lactide) (PDLLA), and any blends thereof. Any derivatives of these which are linked to one or more hydrophilic polymers, for example PEG, PPG and copolymers of PEG and PPG, may also be used.

PLGA is a biocompatible, biodegradable polymer material approved for medical use by the FDA and EMA. PLGA is a co-polymer of lactic acid and glycolic acid, and various forms of PLGA are characterised by the ratio of lactic acid:glycolic acid. Lactic acid can be L-lactic acid, D-lactic acid, or D,L-lactic acid. PLGA degrades when exposed to physiological pH and hydrolyses to form lactic acid and glycolic acid, which are normal by-products of cellular metabolism. The degradation rate of PLGA will vary depending on its molecular weight, the ratio of lactide to glycolide monomers in the polymer chain and the stereochemistry of the monomer subunits. Mixtures of D and L-stereoisomers that disrupt the polymer crystallinity will increase the polymer degradation rate. PLGA or modified PLGA (e.g. PEG derivatives thereof) of different molecular weights may be used and/or having different monomer ratios. Those skilled in the art may select these according to the desired therapeutic use.

The PLGA may have any suitable molecular weight. For example, it may have a weight average molecular weight ranging from 7,000 to 240,000 Da, preferably from 50,000 to 150,000 Da, e.g. from 60,000 to 120,000 Da. The molecular weight of a polymer may be determined using gel permeation chromatography.

The degradation rate of PLGA can be adjusted by altering the lactic acid:glycolic acid ratio. In some embodiments, PLGA for use in accordance with the invention may have a lactic acid:glycolic acid ratio of about 85:15, about 75:25, about 60:40, about 50:50, about 40:60, about 25:75, or about 15:85. In one embodiment, a ratio of about 75:25 may be used.

For use in the invention, the polyethylene imine (PEI) polymer may be linear or branched. In one embodiment, it may be branched. The PEI polymer may have any suitable molecular weight. For example, it may have a weight average molecular weight ranging from 500 to 100,000 Da, preferably from 20,000 to 30,000 Da, e.g. about 25,000 Da. The molecular weight of a polymer may be determined using gel permeation chromatography.

The polymeric matrix comprises an entangled polymeric network of a biocompatible polymer (e.g. PLGA) and PEI polymers. The biocompatible polymer (e.g. PLGA) will comprise the major component of the network, and the PEI will form the minor component. The amount of PEI in the particles as a percentage of the biocompatible polymer (e.g. PLGA) may range from 0.05 to 10 wt. %, preferably from 1 to 5 wt. %, e.g. about 2.1 wt. %

The polymeric particles in accordance with the invention may be polymeric microparticles or polymeric nanoparticles. Particularly preferred are polymeric nanoparticles.

Microparticles will have at least one dimension (e.g. a diameter) which is less than about 1 mm, typically in the range of about 1 to 200 μm. Nanoparticles will have at least one dimension (e.g. a diameter) which is less than about 1 μm, preferably in the range from 10 to 900 nm, more preferably in the range from 50 to 500 nm, e.g. in the range from 100 to 300 nm. The measurement of particle size may be performed using techniques known in the art and described herein. For example, particle sizes may be determined by dynamic light scattering.

It will be understood that the polymeric particles herein described may be anisotropic and non-uniform in nature depending on the method used for their preparation. Substantially monodisperse preparations are generally preferred for use in the invention and these may be produced using the methods herein described. Particulate compositions comprising a plurality of polymeric particles as herein described form a further aspect of the invention. In some embodiments, these may have a polydispersion index (PDI) in the range from 0.01 to 0.5, preferably 0.01 to 0.35, e.g. 0.01 to 0.3. If required, methods and apparatus generally known in the art may be used for separating particles of the sizes defined herein.

Although not wishing to be bound by theory, the presence of the PEI in the polymeric matrix is considered to enhance retention of the desired active agents (i.e. the 'payload'). For example, the anionic or hydrophobic sonosensitiser may be immobilised within the particle by electrostatic attraction to the PEI molecules.

Sonosensitizers which may be used in the invention include compounds which render target cells or tissues hyper-sensitive to ultrasound. In some cases, a sonosensitising agent may be capable of converting acoustic energy (e.g. ultrasound) into ROS that result in cell toxicity. Others may render the target cell or tissues hypersensitive to ultrasound by compromising the integrity of the cell membrane. It is well known that many known sonosensitising agents can facilitate photodynamic activation and can also be used to render cells or tissues hypersensitive to light.

For use in the invention, the sonosensitiser will either be negatively charged or have the potential to exhibit a negative charge, or it will be hydrophobic or have the potential to become hydrophobic. In certain embodiments, a hydrophobic agent may be considered one having a LogP value greater than about 2. Sonosensitizers which have the potential to exhibit a negative charge include those agents which may be modified by reaction with one or more functional groups whereby to introduce the desired net negative charge to the molecule. Sonosensitizers which have the potential to become hydrophobic include those agents whose charge varies dependent on pH. For example, adjustment of the pH environment of the agent may facilitate the formation of an uncharged species which would be considered suitably hydrophobic for incorporation into the polymeric matrix. Alternatively, reaction of the sonosensitiser (e.g. a sonosensitiser containing a quaternary nitrogen) with a suitable functional group or groups (e.g. by acetylation) may result in a net zero charge thereby increasing the hydrophobicity of the molecule.

Examples of compounds suitable for use as sonosensitising agents in the invention include phenothiazine dyes (e.g. methylene blue, toluidine blue), Rose Bengal, porphyrins (e.g. Photofrin®), ATX-70, chlorins, benzochlorins, phthalocyanines, napthalocyanines, porphycenes, cyanines (e.g. Merocyanine 540 and indocyanine green), azodipyromethines (e.g. BODIPY and halogenated derivatives thereof), acridine dyes, purpurins, pheophorbides, verdins, psoralens, hematoporphyrins, protoporphyrins and curcumins. Any known analogues or derivatives of these agents may also be used. Suitable derivatives include the pharmaceutically acceptable salts. Any cationic sonosensitising agents, such as the phenothiazine dyes, may be suitably modified for use in the invention, for example, by acetylation to enhance their hydrophobicity.

Preferred for use as sonosensitizers in the invention are Rose Bengal, indocyanine green (ICG, also known as Cardio Green), and any analogues and derivatives thereof. Particularly preferred for use in the invention is Rose Bengal. ICG has the following structure:

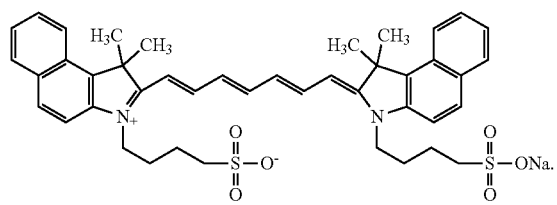

Known analogues of any of the sonosensitizers described herein may also be used in the invention. Particularly suitable are structural analogues of the cyanine-based dyes, e.g. structural analogues of ICG and their pharmaceutically acceptable salts. Examples of these include the cyanine dyes IR820 and IR783, both of which are commercially available:

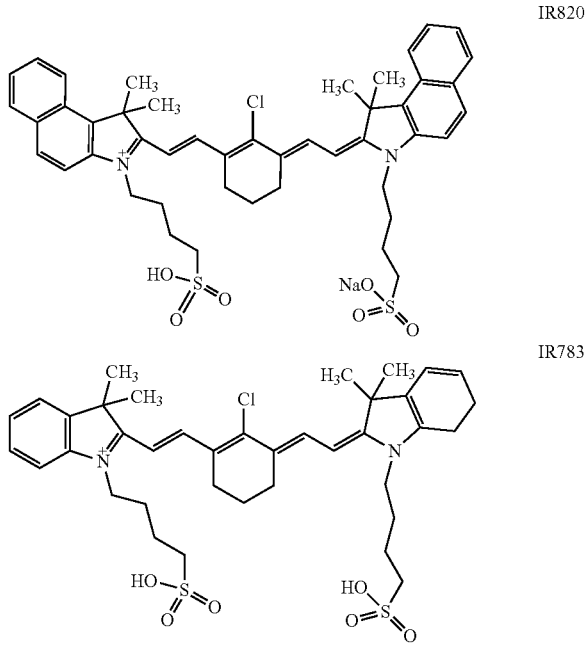

The near-infrared (NIR) absorbing fluorescent dye ICG is FDA approved for use in medical imaging. It absorbs strongly in the NIR region (750-900 nm) and has the advantage that this can be activated by light at a greater depth in human tissue (the penetration of light at 800 nm is four times greater than at 600 nm). However, the singlet oxygen generation (SOG) effectiveness of cyanine dyes such as ICG, IR820 and IR783 is relatively poor when compared to other known sensitizers such as Rose Bengal. Other attempts have been made to improve the ROS generating capability of cyanine dyes by incorporation of halogen atoms (e.g. iodine and bromine) into their structure. For example, in US 2013/0231604 (the entire contents of which are incorporated herein by reference) it is proposed that cyanine-based dyes and analogues of such dyes may be modified by incorporation of three iodine atoms on, the benzene or napthalene portion of each benzazole or napthazole ring. Any of the polymethine dyes (in particular the cyanines) disclosed in this document may be used as sonosensitizers in the present invention. Any of the halogenated analogues of the cyanine dyes (e.g. IR783) described in WO 2017/089800 (the entire contents of which are incorporated herein by reference) may also be used in the invention.

Immunomodulatory agents which are compatible with inclusion in a polymeric particle as herein described and which are thus suitable for use in the invention may readily be determined by those skilled in the art. Charged or non-charged immunomodulatory agents may be employed. Non-limiting examples of such agents include the following:

TLR7 agonists, i.e. agents which stimulate the innate immune system by activating toll-like receptor 7 (TLR7). Examples of such agents include Imiquimod, Resiquimod (also known as R848), Gardiquimod, Poly I:C (Polyinosinic: polycytidylic acid), CpG oligodeoxynucleotides, and Anti-galactosylceramide.

Immunoadjuvants such as indole 2,3 dioxygenase 1 inhibitors (see, for example, Prendergast et al., Cancer Res. 2017 Dec. 15; 77 (24): 6795-6811). Examples of such agents include Indoximod, Epacadostat, and Navoximod.

Low molecular weight immune checkpoint inhibitors, e.g. those having a molecular weight of less than 4,000 Da. Examples of such agents include BMS-1001, BMS-1166, and CCX872 (ChemoCentryx—a CCR2 chemokine receptor inhibitor known to suppress myeloid derived suppressor cells). Other examples of suitable small molecule immune checkpoint inhibitors include any of those described by Sasikumar P G et al. in Small-Molecule Immune Checkpoint Inhibitors Targeting PD-1/PD-L1 and Other Emerging Checkpoint Pathways—BioDrugs (2018) 32:481-497, the entire content of which is incorporated herein by reference (see, in particular, compounds 1-5 in FIG. 1 and compounds 16-40 in Table 1).

Pharmaceutically acceptable salts, derivatives or analogues of any of the above compounds may also be used.

Any imaging agents generally known for use in medical imaging may be embedded in the polymeric particles in accordance with the invention. Suitable agents may readily be selected by those skilled in the art. These include near-infra-red (NIR) imaging agents such as indocyanine green (ICG), and any analogues and derivatives thereof including, but not limited to, those described above in relation to the choice of sonosensitiser for use in the invention. In particular, the following structural analogues of IR783 which are substituted with one or two halogen atoms on each of the benzazole rings may be used as a NIR imaging agent in the invention, as well as their pharmaceutically acceptable salts:

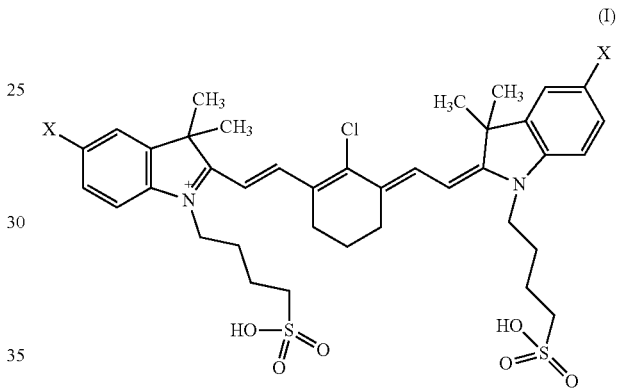

(I)

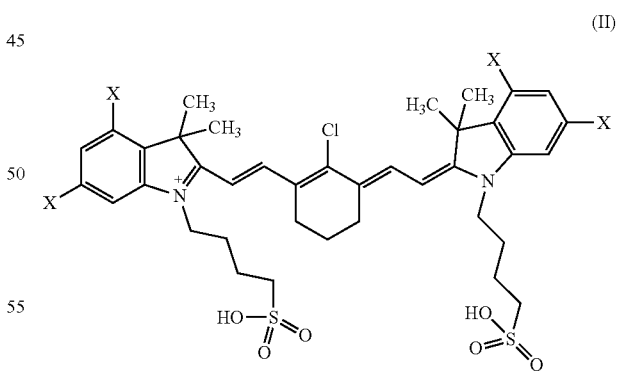

(II)

(wherein in formula I and II, each X is independently selected from a bromine and iodine atom, preferably wherein each X is iodine).

Examples of compounds of formula I and II which may be used in the invention include the following and their pharmaceutically acceptable salts:

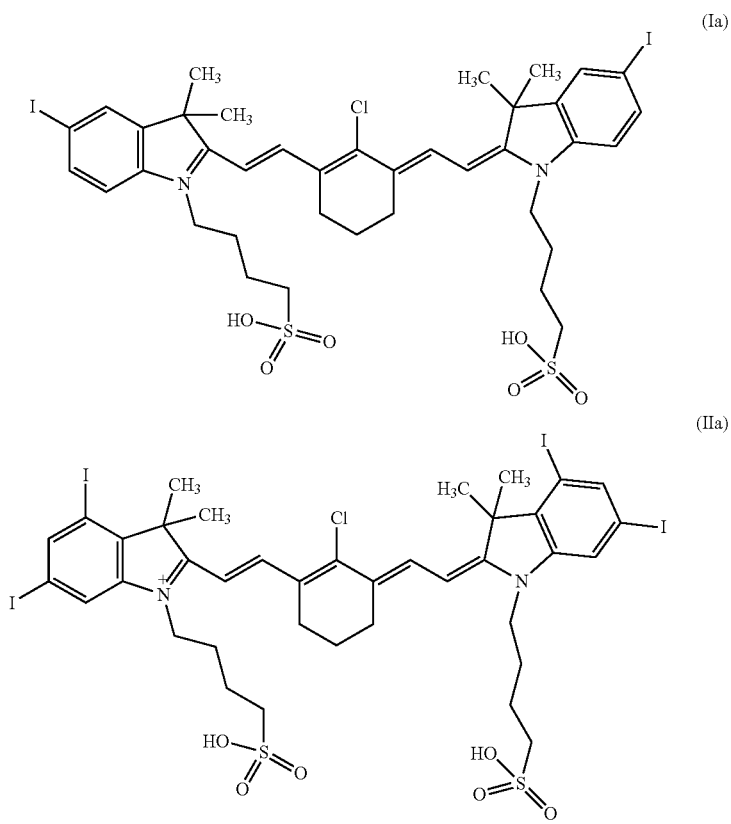

Other imaging agents which may be used include radio-contrast agents, such as diatrizoate and metrizoate which may be used in CT imaging, and Omniscan (gadodiamide) which may be used in MRI. As will be understood, any hollow polymeric capsules herein disclosed, i.e. those containing any gas, including air, may provide acoustic contrast for ultrasound imaging without the need for any additional imaging agent.

The polymeric particles herein described may be prepared using methods known in the art. Polymeric particles may, for example, be prepared using single and double emulsion solvent evaporation, spray drying, solvent extraction, solvent evaporation, phase separation, simple and complex coacervation, and other methods which are well known to those skilled in the art.

Single emulsion solvent evaporation may, for example, be used to prepare polymeric microspheres having a core polymeric matrix. In such methods, the chosen polymer is dissolved in a volatile organic phase comprising an organic solvent. The selected active agent, either in soluble form or dispersed as fine particles, is added to the polymer solution, and the mixture is suspended in an aqueous phase that contains a surfactant such as poly(vinyl alcohol). The aqueous phase may be, for example, a concentration of 1% poly(vinyl alcohol) w/v in distilled water. The resulting emulsion is stirred until most of the organic solvent evaporates leaving solid polymeric microspheres. These may then be washed with water and dried, for example, these may be lyophilised. Polymeric microspheres of different sizes can be obtained by this method. Nanoparticles can be obtained in the same manner as microparticles except that high speed mixing or homogenisation (e.g. by sonication) is used to reduce the size of the emulsions to less than about 1 μm.

In a double emulsion solvent evaporation method, a water-in-oil emulsion comprising a dispersion of an aqueous phase (in which the active agent is dissolved or dispersed) in an organic phase (in which the polymer is dissolved) may be added to a second aqueous solution containing a surfactant. Stirring or sonication generates a water-in-oil-in-water double emulsion which is then stirred to evaporate the organic solvent. Centrifugation to remove the supernatant results in polymeric microspheres or nanospheres in which the active agent is embedded. An example of a double emulsion method is described in Castro et al. (Journal of Colloid and Interface Science 518 (2018): 122-129), the entire content of which is incorporated herein by reference.

For use in preparing the polymeric particles herein described, the organic phase may contain any organic solvent or mixture of solvents in which PLGA is soluble. Suitable solvents include, but are not limited to, acetone, methylene chloride, ethyl acetate, and benzyl alcohol. In a particular embodiment, the solvent is acetone. The PEI may be dissolved or dispersed in the same solvent.

The double emulsion method used by Castro et al. is complex. As described in the examples herein, the inventors have developed a modification of the known single emulsion solvent evaporation technique to produce the polymeric particles. In this method, PLGA is dissolved in acetone and PEI is dispersed in acetone. The selected active agent (or agents) are each dissolved in an alcohol solvent (e.g. ethanol or methanol). The organic solutions are combined and added to an aqueous phase containing a surfactant such as poly (vinyl alcohol). The aqueous phase may be, for example, a concentration of 1% poly(vinyl alcohol) w/v in distilled water. During dropwise addition of the combined organic solutions to the aqueous phase, emulsification is achieved by sonication using an ultrasound probe. Thereafter, the resulting emulsion is stirred (e.g. overnight) until the organic solvents have evaporated to leave the solid polymeric nanoparticles. These may be recovered by centrifugation, washed and dried.

Other emulsifiers may be also be used in the methods herein described, including non-ionic surfactants, cationic surfactants, anionic surfactants and amphoteric surfactants. Preferably, the emulsifier may be PVA. The aqueous emulsifier solution is prepared by dissolving an emulsifier in water. In the invention, an aqueous solution of polyvinyl alcohol (PVA) is preferred for use as the aqueous emulsifier solution. PVA functions as a surfactant to stabilise the resulting polymeric particles. Examples of other emulsifiers that may be used include, but are not limited to, polyalcohol derivatives such as glycerine monostearate, non-ionic surfactants such as sorbitan esters and polysorbates, cationic surfactants such as cetyltrimethyl ammonium bromide, anionic surfactants such as sodium lauryl sulfate, and amphoteric surfactants such as polyaminocarboxylic acids.

By way of example, the following procedure may be used to prepare polymeric nanoparticles containing a sonosensitiser: poly(D,L-lactic-co-glycolic acid) (PLGA) (75:25, molecular weight: 66,000-107,000) is dissolved in acetone, polyethylene imine (PEI) (branched, molecular weight: 25,000) is added to acetone, and the sonosensitiser is dissolved in ethanol. For generation of the polymeric nanoparticles, the solutions are combined and added dropwise to an aqueous solution of polyvinyl alcohol (PVA) (e.g. 1% PVA (87-90% hydrolysed, molecular weight: 30,000-70,000)). During addition of the combined solutions to the PVA, efficient emulsification may be achieved by exposure of the PVA solution to low frequency ultrasound, e.g. by sonication using a 6 mm ultrasound probe (Vibra-Cell), delivering ultrasound at a frequency of 20 kHz, operated at 70% amplitude. Following dispersion, stirring may be carried out whilst allowing the solvent to evaporate at normal pressure and room temperature to form the desired nanoparticles containing the embedded sonosensitiser. The polymeric nanoparticles may then be recovered by filtration or centrifugation followed. Washing, for example using distilled water and/or phosphate buffered saline (PBS), provides the final polymer particles. If desired, these may by re-suspended in distilled water for storage or, more preferably, lyophilised for storage.

For the preparation of polymeric particles which carry additional active agents, i.e. an immunomodulatory agent and/or an imaging agent, these may similarly be dissolved or dispersed in appropriate organic solvents prior to formation of the desired emulsion. For example, the imaging agent (e.g. ICG) may be dissolved in ethanol, and the immunomodulatory agent (e.g. imiquimod) may be dissolved in methanol.

Polymeric capsules, i.e. microcapsules or nanocapsules, having a shell composed of the polymeric matrix may be prepared using similar methods, such as a double emulsion method. For example, these may be prepared using a modification of the water-in-oil-in-water emulsion method which is used for the preparation of PLGA microbubbles and described in McEwan et al. (Langmuir (2014) 30:14926-14930, the entire content of which is incorporated herein by reference). A first emulsion may be prepared by combining an aqueous solution of ammonium carbonate with an organic solvent (e.g. dichloromethane, acetone, etc.) in which the biocompatible polymer (e.g. PLGA) is dissolved and PEI is dispersed. High speed mixing or sonication of the mixture provides a first emulsion which is then added to a second aqueous phase containing a surfactant such as poly (vinyl alcohol). Homogenisation of the resulting mixture results in a water-in-oil-in-water emulsion to which isopropanol alcohol is added in order to harden the particles and this is followed by further stirring. The microcapsules may be recovered by centrifugation, washed and then lyophilised. This results in hollow capsules with the shell comprising the polymers and active agent(s). In a modification of this method, a water soluble active agent may be dissolved in the ammonium carbonate solution during particle preparation in order to deposit the active agent in the hollow particle core. This approach may be particularly suitable for active agents which could be inactivated in an organic solvent.

Polymeric particles obtained or obtainable by any of the methods herein described form a further aspect of the invention.

The polymeric particles herein described are suitable for the treatment of disorders or abnormalities of cells or tissues within the body which are responsive to sonodynamic therapy. These include malignant and pre-malignant cancer conditions, such as cancerous growths or tumours, and their metastases; tumours such as sarcomas and carcinomas, in particular solid tumours. The invention is particularly suitable for the treatment of tumours, especially those which are located below the surface of the skin.

Non-limiting examples of tumours that may be treated using the polymeric particles herein described are sarcomas, including osteogenic and soft tissue sarcomas; carcinomas, e.g. breast, lung, cerebral, bladder, thyroid, prostate, colon, rectum, pancreas, stomach, liver, uterine, hepatic, renal, prostate, cervical and ovarian carcinomas; lymphomas, including Hodgkin and non-Hodgkin lymphomas; neuroblastoma, melanoma, myeloma, Wilm's tumour; leukemias, including acute lymphoblastic leukaemia and acute myeloblastic leukaemia; astrocytomas, gliomas and retinoblastomas. In particular, the following tumours and any associated metastatic condition may be treated: pancreatic cancer, breast cancer, prostate cancer, glioma, non-small cell lung carcinoma, head and neck cancers, cancers of the urinary tract, kidney or bladder, advanced melanoma, oesophageal cancer, colon cancer, hepatic cancer, and lymphoma. Metastatic disease, micrometastatic disease or CTCs arising from any of these tumours may also be treated using any of the polymeric particles herein described. The treatment of pancreatic cancer, and in particular metastatic pancreatic cancer, forms a preferred aspect of the invention.

As described herein, the inventors have observed that treatment of a targeted, primary tumour using a polymeric particle according to the invention is capable of producing a systemic abscopal effect. As a result of this observation, the polymeric particles herein described also find use more generally in the treatment of subjects having metastatic cancer, micrometastatic cancer, CTCs, or multiple primary tumours.

In another aspect, the invention thus provides a polymeric particle as herein described for use in a method of sonodynamic treatment of a metastatic disease, micrometastatic disease, CTCs, or in the treatment of multiple primary tumours. Corresponding methods of medical treatment also form part of the invention. In another aspect the invention thus also provides a method of sonodynamic treatment of a metastatic disease, micrometastatic disease, CTCs, or multiple primary tumours in a subject (e.g. a patient), said method comprising the step of administering to affected cells or tissues of a subject in need thereof a polymeric particle as herein described and subjecting said cells or tissues to ultrasound irradiation.

In such methods which rely on the abscopal effect, the subject may have a plurality of tumours in at least two body tissues (e.g. in at least two organs of the body). In some embodiments, the methods will involve selection of a tumour for sonodynamic treatment, for example selection of the tumour that is the most anatomically accessible to SDT, or which has the best chance of producing a systemic abscopal effect following sonodynamic treatment with a polymeric particle as herein described. In many cases this will be the primary tumour. In such a method, the polymeric particle and ultrasound will therefore be targeted to the primary tumour (or the organ which bears the primary tumour). For example, where the subject is suffering from pancreatic cancer, SDT may be targeted to the pancreas.

In some embodiments, any of the methods herein described may involve the initial step of determining the location and/or extent (e.g. volume) of at least two tumours in different tissues (e.g. in different organs) of the subject. Such methods are well known in the art and may include, for example, positron emission tomography (PET) scans, X-ray computerised tomography (CT) scans, MRI scans, or any combination thereof.

The methods herein described can therefore be used to treat a subject having two or more tumours in different tissues (e.g. organs) by identifying the best tumour (or tumour-bearing tissue, e.g. organ) to treat and inducing an abscopal effect that treats other tumours or cancerous cells in non-adjacent tissues or organs. In some cases, the other tumours or cancerous cells may be metastatic tumours or micrometastatic tumours, or they may be CTCs. However, in other embodiments, the other tumours may be other primary tumours. In such methods, at least one of the tumours is treated by targeted SDT using a polymeric particle as herein described.

As described herein, the inventors have observed that treatment of a targeted, primary tumour in a subject (e.g. a patient) using a polymeric particle according to the invention is also capable of inducing a protective immune memory in the subject which minimises their risk of developing of secondary lesions. In another aspect, the invention thus provides a polymeric particle as herein described for use in a method of prevention of secondary lesions in a subject (e.g. a patient). Corresponding methods of medical treatment also form part of the invention.

For use in any of the methods herein described, the polymeric particles will generally be provided in a pharmaceutical composition together with at least one pharmaceutically acceptable carrier or excipient. Such pharmaceutical compositions may be formulated using techniques well known in the art. The route of administration will depend on the intended use. Typically, these will be administered systemically and may thus be provided in a form adapted for parenteral administration, e.g. by intradermal, subcutaneous, intraperitoneal or intravenous injection. Suitable pharmaceutical forms include suspensions and solutions which contain the active polymeric particles together with one or more inert carriers or excipients. Suitable carriers include saline, sterile water, phosphate buffered saline and mixtures thereof. The compositions may additionally include other agents such as emulsifiers, suspending agents, dispersing agents, solubilisers, stabilisers, buffering agents, wetting agents, preserving agents, etc. The compositions may be sterilised by conventional sterilisation techniques. Solutions containing the particles may be stabilised, for example by the addition of agents such as viscosity modifiers, emulsifiers, solubilising agents, etc.

Preferably, the pharmaceutical compositions for use in the invention will be used in the form of an aqueous suspension of the polymeric particles in water or a saline solution, e.g. phosphate-buffered saline. The particles may be supplied in the form of a lyophilised powder for reconstitution at the point of use, e.g. for reconstitution in water, saline or PBS.

The methods herein described involve administration of a pharmaceutically effective amount of the composition which contains the selected polymeric particles. The particles may then be allowed to distribute to the desired portion or target area of the body prior to activation of the sonosensitiser. Once administered to the body, the target area is exposed to ultrasound at a frequency and intensity to achieve the desired therapeutic effect. The effective dose of any of the compositions herein described will depend on the nature of the particles, the mode of administration, the condition to be treated, the subject (e.g. patient), etc. and may be adjusted accordingly.

The timing of ultrasound delivery to achieve the desired effects needs to take into account various factors including the nature (size, shape, etc.) of the particles, the cells to be treated and the quantity of particles taken up by the cells or tissues (which, in turn, will depend on the efficacy of the EPR for that particular tumour), the nature of the active agents, the environment of the cells, and whether administration is direct to the target tissue or at a distal site, etc. Taking these considerations into account appropriate timings may readily be determined by those skilled in the art.

The frequency and intensity of the ultrasound which may be used can be selected based on the need to achieve sonoactivation of the sonosensitser. Ultrasound frequencies will typically be in the range 20 kHz to 10 MHz, preferably 0.1 to 2 MHz. Ultrasound may be delivered as either a single frequency of a combination of different frequencies. Intensity (i.e. power density) of the ultrasound may range from about 0.1 W/cm$^2$ to about 1 kW/cm$^2$, preferably from about 1 to about 50 W/cm$^2$. Treatment times will typically be in the range of 1 ms to 20 minutes and this will be dependent on the intensity chosen, i.e. for a low ultrasound intensity the treatment time will be prolonged and for a higher ultrasound intensity the treatment time will be lower. Ultrasound may be applied in continuous or pulsed mode and may be either focused or delivered as a columnar beam. Ultrasound may also be provided at multiple frequencies, either simultaneously or sequentially, e.g. 20 kHz together with 1 MHz or 20 kHz followed by 1 MHz, respectively. Alternatively, ultrasound may be delivered in a modulated mode with respect to frequency and/or amplitude.

Any radiation source capable of producing acoustic energy (e.g. ultrasound) may be used in the methods herein described. The source should be capable of directing the energy to the target site and may include, for example, a probe or device capable of directing energy to the target tissue from the surface of the body.

In the case where the sonosensitiser used is one which also responds to light, ultrasound activation may be accompanied by light activation. Photothermal activation may also additionally be employed, for example when using a NIR dye as the sonosensitiser.

Any of the polymeric particles herein described may be used in a method of combination therapy in which they are administered to a subject (e.g. a patient) in combination with a separate immune checkpoint inhibitor.

In another aspect the invention thus provides a polymeric particle as herein described for use in a method of sonodynamic therapy comprising simultaneous, separate or sequential use of an immune checkpoint inhibitor.

In another aspect the invention provides a method of sonodynamic therapy which comprises at least the following steps:
(a) administering a polymeric particle as herein described to affected cells or tissues of a subject in need thereof (e.g. a patient) and subjecting said cells or tissues to ultrasound irradiation; and
(b) simultaneously, separately or sequentially administering to said subject (e.g. said patient) a pharmaceutically effective amount of an immune checkpoint inhibitor.

When used in combination therapy, the polymeric particle and immune checkpoint inhibitor may be administered to the subject (e.g. a patient) separately, simultaneously or sequentially. Where they are administered sequentially, they may be administered in either order. In one embodiment, the immune checkpoint inhibitor is administered prior to the polymeric particle. For example, it may be administered up to several hours or even several days prior to administration of the polymeric particle. In particular, the immune checkpoint inhibitor may be administered from 1 hour to 5 days, e.g. from 2 hours to 3 days, before the polymeric particle is administered and SDT is carried out.

In an embodiment of the invention, the polymeric particle and immune checkpoint inhibitor will be administered separately from one another, preferably sequentially.

A product comprising a polymeric particle as herein described and an immune checkpoint inhibitor for simultaneous, separate or sequential use in a method of sonodynamic therapy also forms part of the invention.

Also provided herein is a kit (or pharmaceutical pack) comprising the following components: (i) a polymeric particle as herein described; and separately (ii) an immune checkpoint inhibitor; optionally together with (iii) instructions for the use of said components in a method of sonodynamic therapy.

For simultaneous administration, the polymeric particle and immune checkpoint inhibitor may be provided together in a single formulation. In another aspect, the invention thus provides a pharmaceutical composition comprising a polymeric particle as herein described and an immune checkpoint inhibitor, together with at least one pharmaceutical carrier or excipient.

Any compound capable of inhibiting the normal immunosuppressive function of an immune checkpoint may be used as an "immune checkpoint inhibitor". In one embodiment, the immune checkpoint inhibitor is an antibody that binds to a specific immune checkpoint molecule whether that immune checkpoint molecule is itself a receptor or a ligand therefor. Receptors which form part of an immune checkpoint are typically found on the surface of T-cells. Those skilled in the art can readily determine agents which may function as an inhibitor of a specific immune checkpoint target. Suitable inhibitors may, for example, be selected from the group consisting of proteins, peptides, peptidomimetics, peptoids, antibodies, antibody fragments, small inorganic molecules, small non-nucleic acid organic molecules or nucleic acids such as anti-sense nucleic acids, small interfering RNA (siRNA) molecules, oligonucleotides, and any combination thereof. The inhibitor may, for example, act to down regulate expression of an immune checkpoint molecule. The inhibitor may, for example, be a modified version of the natural ligand, such as a truncated version of one of the ligands. It may be naturally occurring, recombinant or synthetic.

In one embodiment, the immune checkpoint inhibitor may be an antibody which inhibits a particular immune checkpoint molecule. Inhibitors of cytotoxic T-lymphocyte-associated antigen-4 (CTLA-4), programmed cell death-1 (PD-1) and its ligand, PDL-1, are preferred, for example antibodies thereto.

Immune checkpoint inhibitors for use in the invention include, but are not limited to, inhibitors of PD-1, PDL-1, CTLA-4, LAG-3 (Lymphocyte Activation Gene-3) and TIM-3 (T-cell Immunoglobulin Mucin-3). In one embodiment, the immune checkpoint inhibitor is a PD-1 inhibitor, a PDL-1 inhibitor, or a CTLA-4 inhibitor. Examples of such drugs are known and used in the art and any may be suitable for use in the invention.

Examples of PD-1 inhibitors which may be used in the invention include, but are not limited to, nivolumab (Opdivo), pembrolizumab (Keytruda), spartalizumab, TSR-042, atezolizumab (MPDL3280A), avelumab, and duravlumab. Other examples include BMS-1001 and BMS-1166 developed by BMS (see Skalniak et al., Oncotarget, 2017; 8 (42): 72167-72181, the entire content of which is incorporated herein by reference), and SB415286 (see Taylor et al., Cancer Res. 2018, 78 (3), 706-717, the entire content of which is incorporated herein by reference). Non-limiting examples of CTLA-4 inhibitors which may be used in the invention include ipilimumab (Yervoy), and tremelimumab.

Any combination of known immune checkpoint inhibitors may also be used in the invention.

The immune checkpoint inhibitor will generally be administered in the form of a pharmaceutical composition containing suitable carriers and/or excipients, such as any of those herein described in relation to the polymeric particle. Typically the immune checkpoint inhibitor will be formulated for intravenous injection, although other modes of delivery such as intralesional or intraperitoneal administration may also be used. A suitable dosage of the immune checkpoint inhibitor can readily be selected by those skilled in the art having in mind factors including the nature of the condition to be treated and its severity.

The invention will now be described further with reference to the following non-limiting Examples and the accompanying figures in which:

FIG. 1 shows ROS production by RB, RB+ICG or RB+ICG+IM containing nanoparticles in the presence and absence of ultrasound (US). Error bars represent ± the SD and n=3.

FIG. 2 shows nIR fluorescence imaging based study demonstrating particle uptake by pancreatic cancer cells (BxPC3). The inset shows a typical fluorescence image from which the data were derived. Error bars represent ± SD where n=3.

Figure 6:
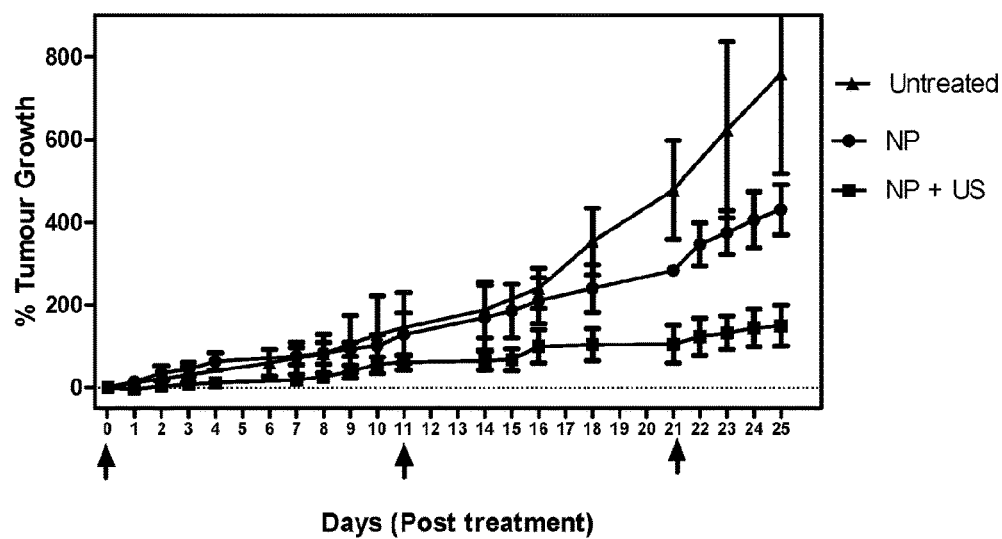

FIG. 6 shows the treatment of human pancreatic xenograft tumours in SCID mice using RB+ICG nanoparticles (NP) in the present and absence of ultrasound (US). Arrows indicate treatment times. Error bars represent ± SD, where n=3 for NP, n=4 for untreated and n=4 for NP+US.

Figure 7:
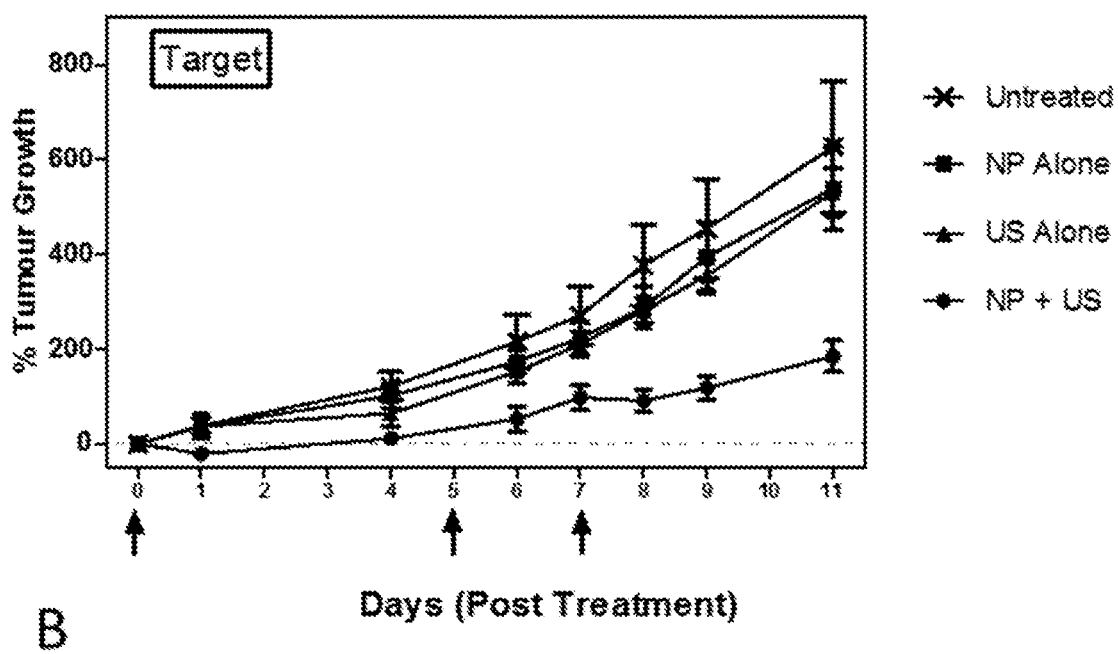
Figure 7:
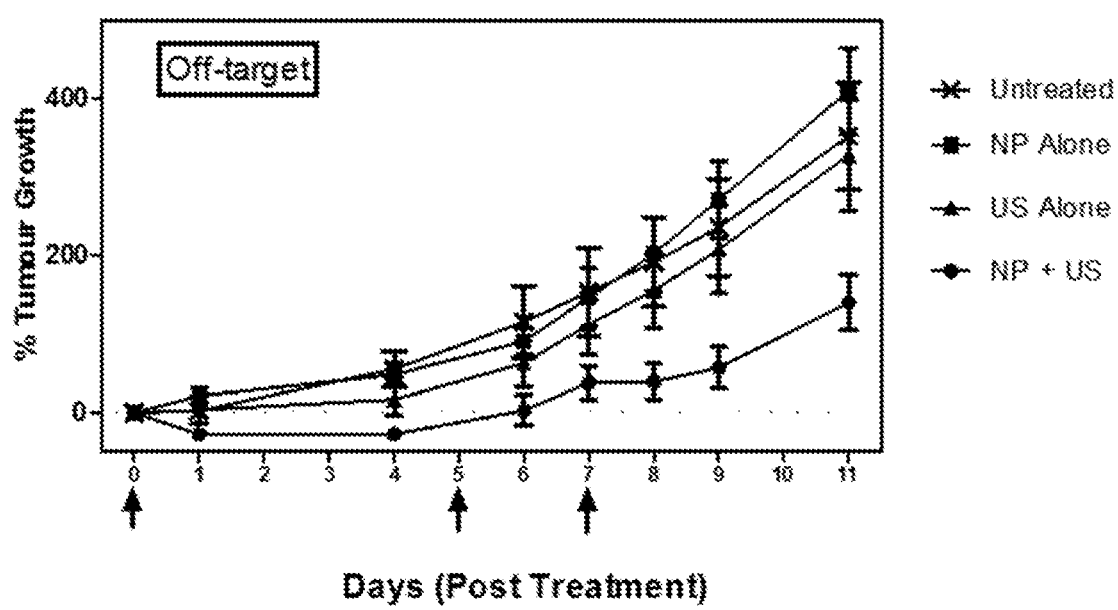

FIG. 7 demonstrates an SDT-mediated abscopal effect in animals bearing multiple tumours. Target tumours (A) were treated with nanoparticles alone (NP), ultrasound alone (US) and a combination of each. Growth of the off-target tumour (B) from each group of animals was also monitored. Arrows indicate treatment times for the targeted tumour. Error bars represent ± SEM and n=5 for each group.

Figure 8:
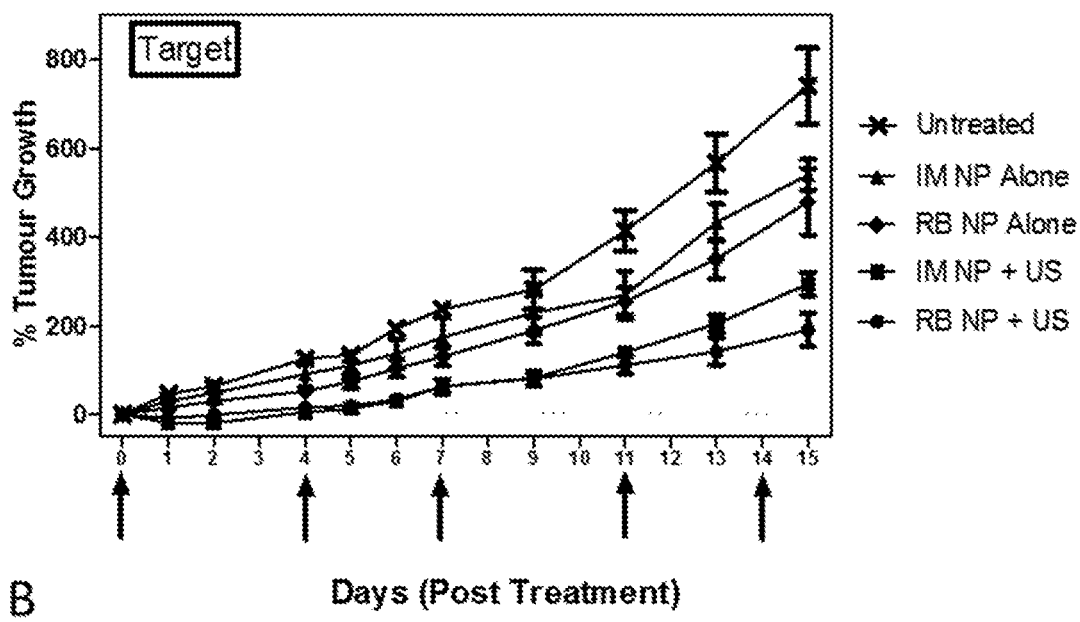
Figure 8:
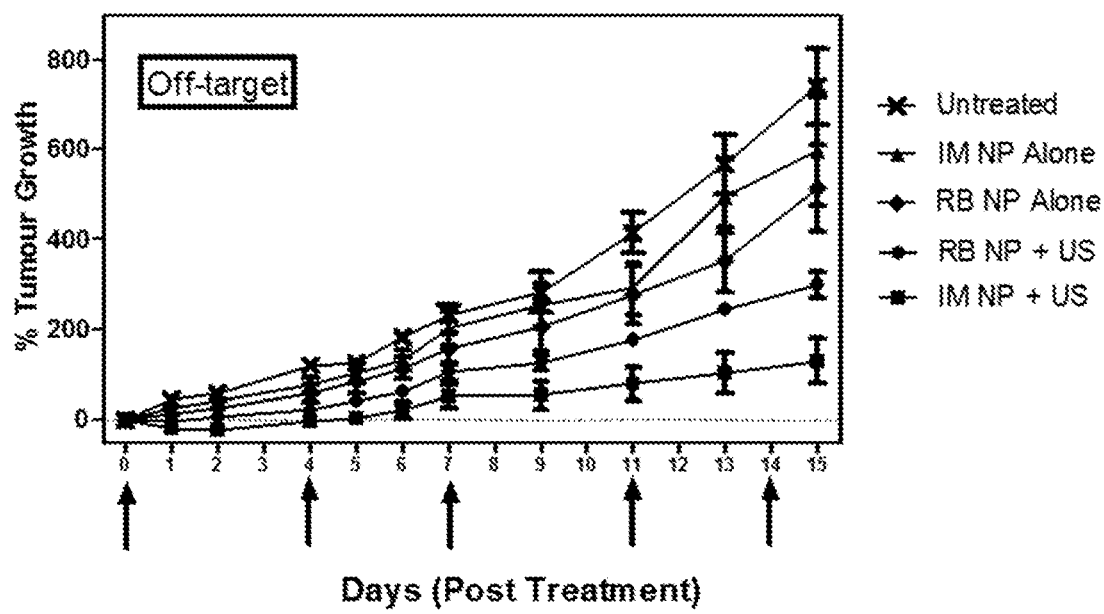

FIG. 8 shows the comparative effect of RB+ICG (RB NP)- and RB+ICG+IM (IM NP)-mediated SDT on target and off-target tumours in the same animal. Arrows indicate the treatment times for the target tumour. Error bars represent ± SEM and for the untreated control n=17, IM NP alone n=3, IM NP+US n=5, RB NP alone n=4, RB NP+US n=4.

Figure 9:
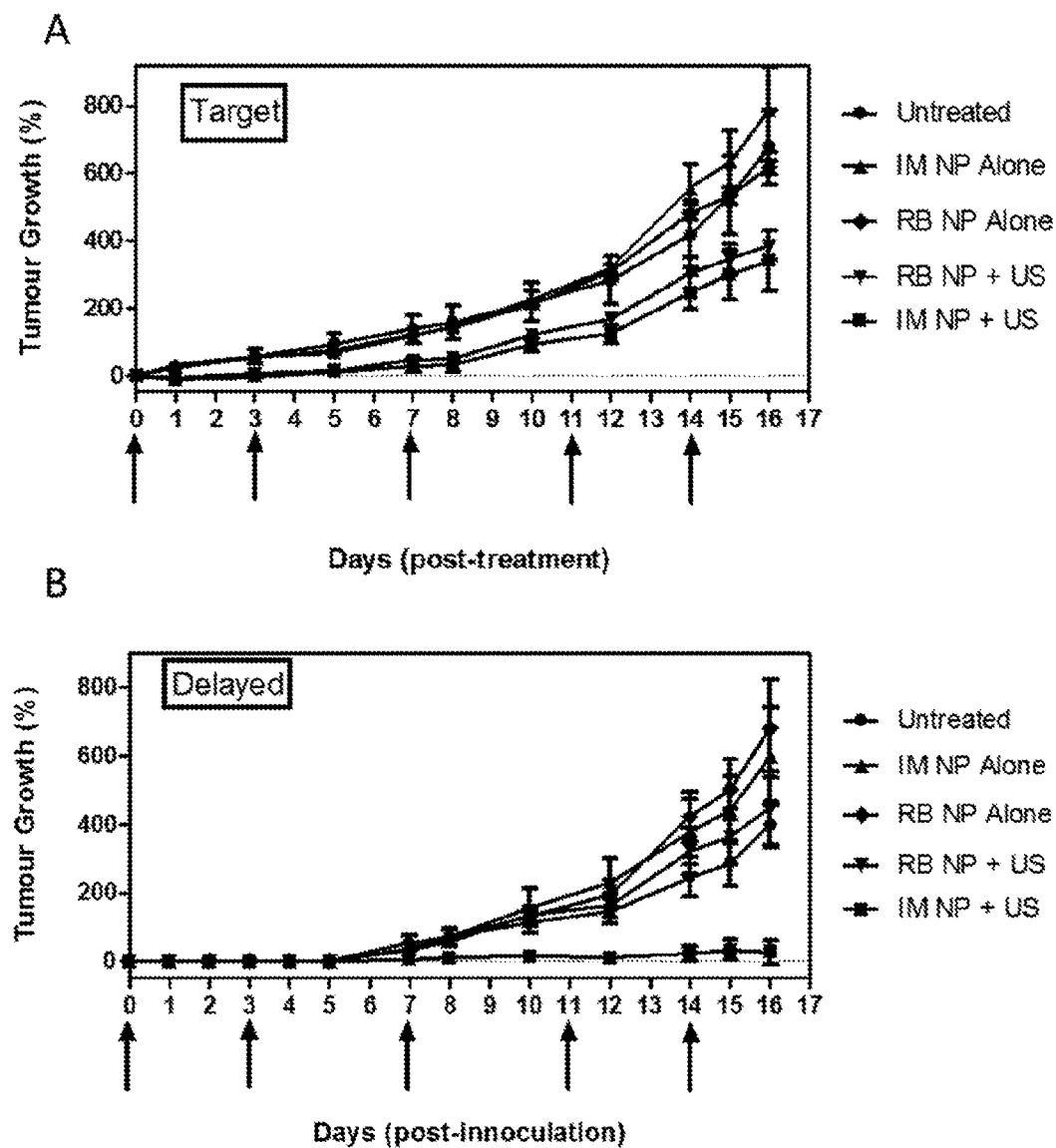

FIG. 9 shows the protective effect provided against tumour establishment by RB+ICG+IM (IM NP)-mediated SDT. For comparative purposes, tumours were also treated with RB+ICG (RB NP)-mediated SDT. Arrows indicate treatment times at the target tumours. Error bars represent ± SEM and for the untreated control n=3, IM-US n=4, IM+US n=3, RB-US n=4, RB+US n=5.

Figure 10:
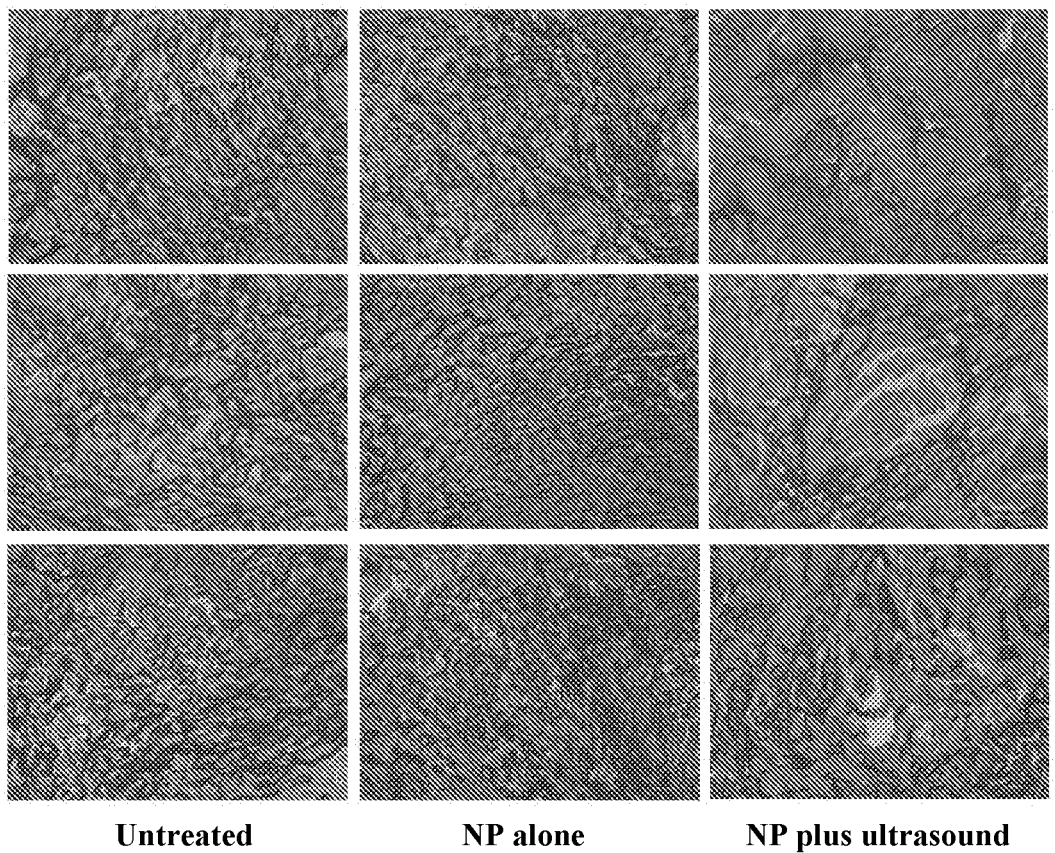

FIG. 10 shows the staining of residual tumour tissues for stroma (intense red colour—shown as dark grey) using Sirius Red. Magnification=50.

Figure 11:
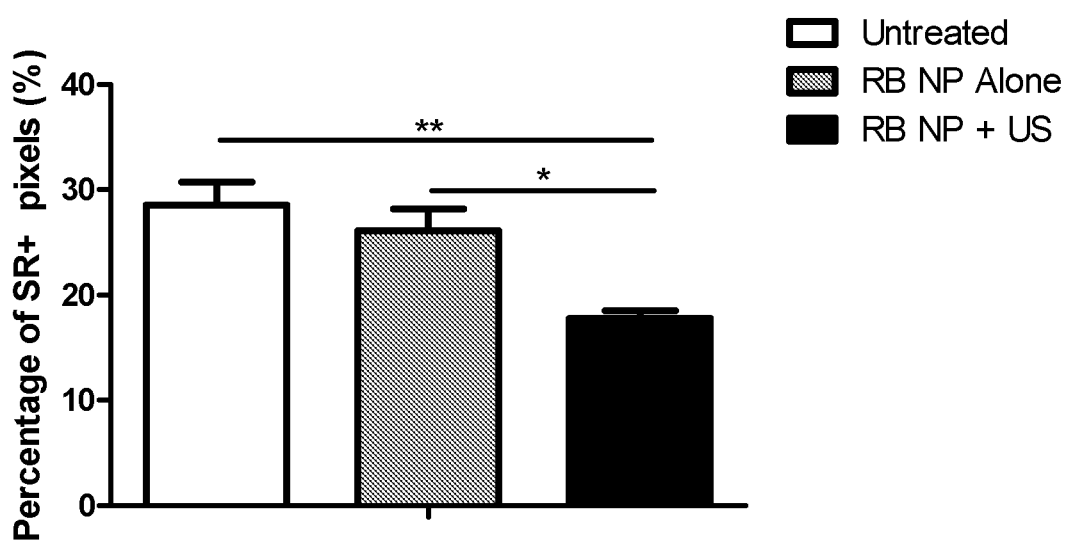

FIG. 11 shows the percentage of red pixels (stroma) per section frame in FIG. 10 where error bars represent ± SEM; n=4 and * p<0.05 and ** P<0.01.

Figure 12:
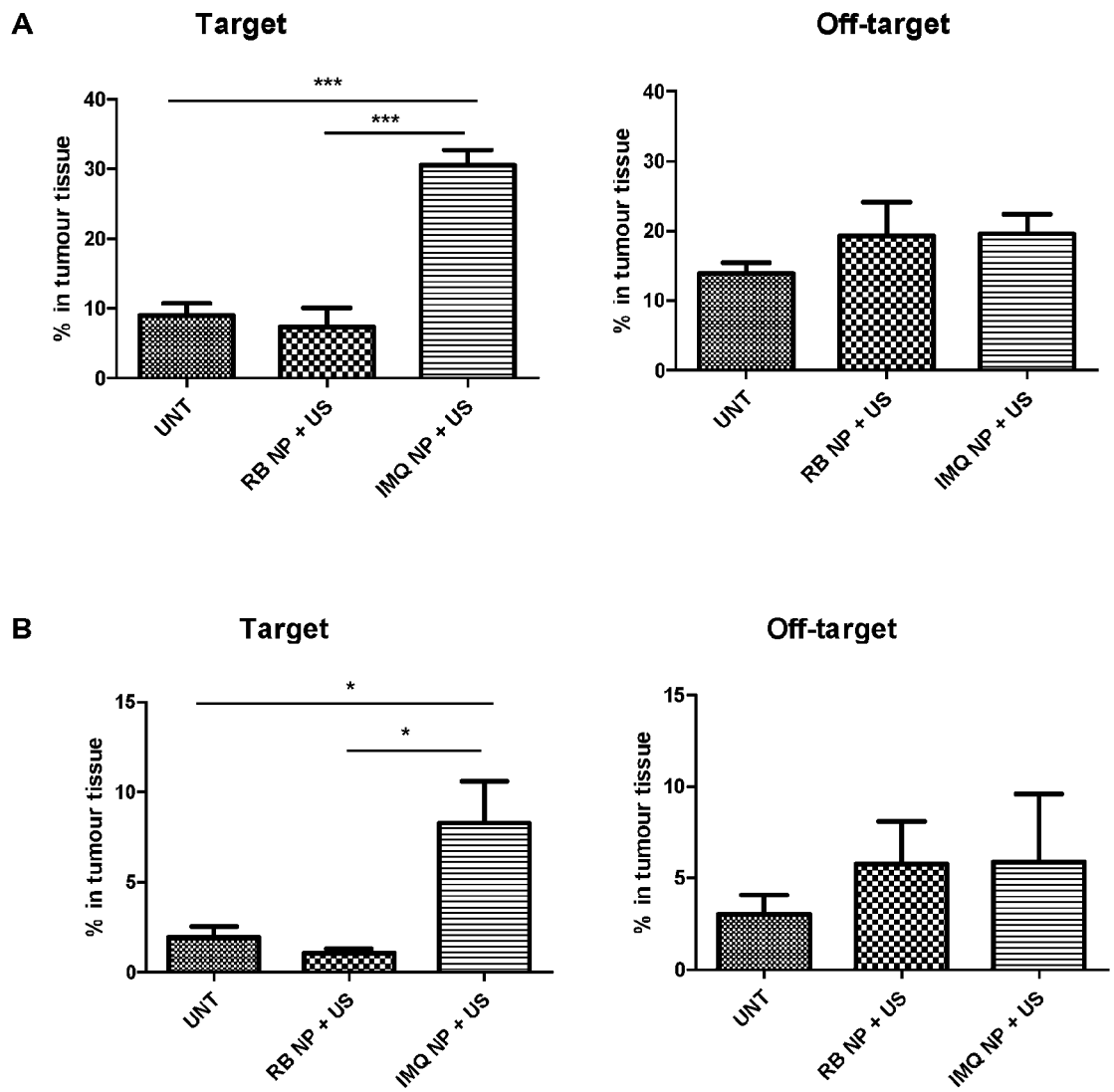

FIG. 12 shows tumour infiltrating (A) leukocytes (CD45$^+$) and (B) cytotoxic T cells (CD8a*) in target and off-target tumours receiving no treatment (UNT), treated with RB and ICG containing nanoparticles plus ultrasound (RB NP+US) and treated with RB, ICG and imiquimod-containing nanoparticles plus ultrasound (IM NP+US). Error bars represent ±SEM where n=4 and * p<0.05, *** p<0.001.

EXAMPLES

Example 1—Nanoparticle Preparation and Characterisation 1.1 Nanoparticle Preparation:

The following procedure was used to prepare nanoparticles containing Rose Bengal (RB), containing Rose Bengal plus indocyanine green (RB+ICG) or containing Rose Bengal, indocyanine green and imiquimod (RB+ICG+IM). 60 mg of poly(DL-lactic-co-glycolic acid) (PLGA) (75:25, MW 66,000-107,000) was dissolved in 2 mL acetone. A 1.25 mg aliquot of polyethylenimine (PEI) (branched, MW 25,000) (1.25 mg/mL) was added to 4 mL of acetone. For RB nanoparticles, 10 mg RB was dissolved in 2 ml ethanol. For RB+ICG nanoparticles, the ICG was dissolved in ethanol at a concentration of 1 mg/mL and for RB+ICG+IM nanoparticles, the IM was dissolved at a concentration of 1 mg/mL in methanol. For generation of the relevant nanoparticles the appropriate payload solution or combination of solutions were added dropwise to 40 mL of 1% polyvinyl alcohol (PVA) (87-90% hydrolysed, MW 30,000-70,000). During addition of the payload solutions to the PVA, efficient emulsification was ensured by sonication using a 6 mm ultrasound probe (Vibra-Cell), at a frequency of 20 kHz, operated at 70% amplitude for 6 min. after which the suspension was stirred overnight to ensure solvent removal. Nanoparticles were recovered by centrifugation at 10,500 rpm for 20 minutes and then washed, firstly, with distilled water and then phosphate buffered saline (PBS). The pellets were re-suspended in 3 ml distilled water and lyophilised for storage.

1.2 Nanoparticle Characterisation:

Nanoparticle size was determined using dynamic light scattering using a Malvern Zetasizer (Malvern Instruments, UK). Particles were suspended at a concentration of 1 mg/mL in distilled water and both the size and polydispersion index was determined for each type of particle. The results are summarised in Table 1 and demonstrate that the particles ranged in size from 226 to 263 nm, which is compatible with exploiting the tumour enhanced permeability and retention (EPR) effect. In addition, the particles had relatively low PDIs indicating a relatively monodisperse preparation.

TABLE 1

| DLS analysis of nanoparticles | | |
|---|---|---|
| Sample | Diameter (nm) | PDI |
| RB | 235-258 | 0.03-0.2 |
| RB + ICG | 231-263 | 0.03-0.2 |
| RB + ICG + IM | 226-259 | 0.09-0.16 |

To determine the loading efficiency (LE) of RB, ICG and IM, the relevant particles were dissolved in dimethyl sulfoxide (DMSO) and the concentrations of each payload were determined by measuring the absorbance at 565 nm and 790 nm, respectively. The loading efficiency of IM was determined using HPLC. The loading efficiency is expressed as the mass of the relevant payload as a % of the theoretical maximum possible. The data obtained are shown in Table 2.

TABLE 2

| Loading efficiencies of payloads into nanoparticles. | | | |
|---|---|---|---|
| Sample | LE (RB)% | LE (ICG)% | LE (IM)% |
| RB | 47.2 | 0 | 0 |
| RB + ICG | 36.1 | 26.8 | 0 |
| RB + ICG + IM | 38.8 | 26.4 | 20.5 |

Example 2—Preparation of RB Nanoparticles in the Presence and Absence of PEI

In order to demonstrate the value of incorporating PEI into the formulation, RB particles were prepared in the presence and absence of PEI. Following preparation, both formulations were visually compared. The preparation containing PEI was more intensely coloured and clearly demonstrated that these particles contained more RB.

Example 3—Ultrasound-Mediated Reactive Oxygen Species Generation

In order to demonstrate that particles were capable of generating reactive oxygen species (ROS) when exposed to ultrasound, thereby demonstrating their potential for use in SDT, particles (RB or RB+ICG or RB+ICG+IM) were suspended at a concentration of 1 mg/mL in phosphate buffered saline (PBS). 2 mL of this was added to 50 mL of 10 μM 1,3-diphenylisobenzofuran (DPBF) prepared in a water/ethanol mixture (50:50) which had been aerated for 10 min. During exposure to ultrasound at a frequency of 1

Figure 1:
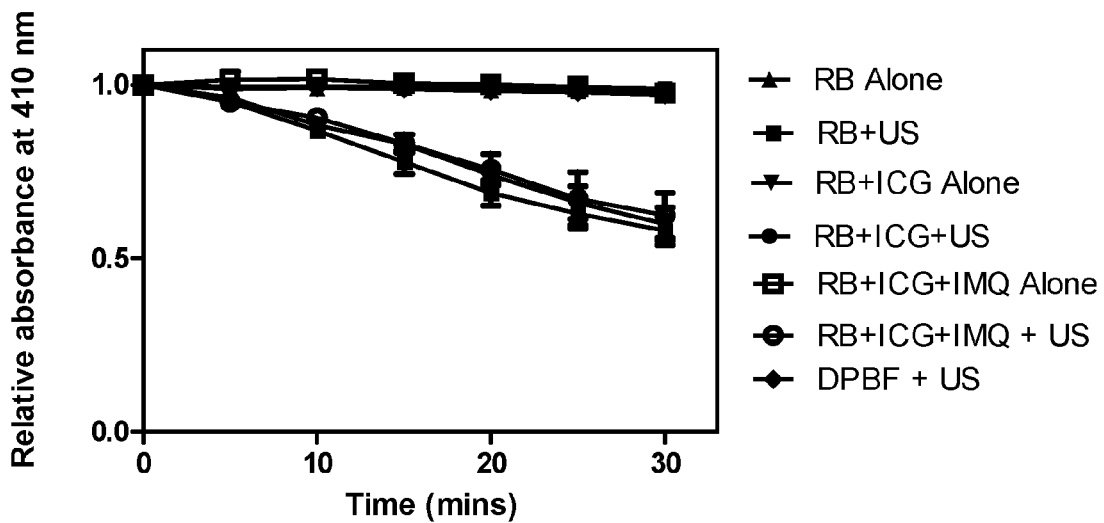

MHZ, a power density of 3.5 W/cm², a duty cycle of 50% (at a pulse repetition frequency of 100 Hz) for 30 min, 1 mL samples were harvested at 5 min intervals and the absorbance at 410 nm was determined to assess the oxidative bleaching of DBPF. The results are shown in FIG. 1 and they demonstrate that the particles are able to generate ROS in the presence of ultrasound. The results also confirmed the potential of these particles for use in SDT.

Figure 2:
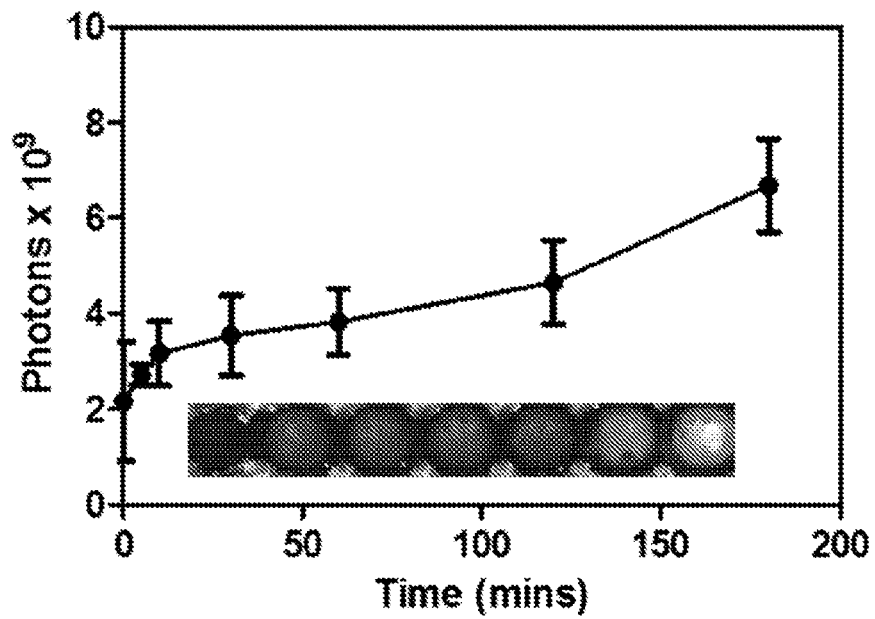

Example 4—Nir Fluorescence Imaging to Monitor Cellular Uptake of RB+ICG Nanoparticles In order to demonstrate that incorporating ICG could provide a nIR imaging capability, the cellular uptake of RB+ICG particles using nIR imaging was assessed. $5 \times 10^3$ human pancreatic cancer cells (BxPC3) were plated into each well of a 96-well plate in RPMI 1640 medium supplemented with 10% (v/v) fetal bovine serum and cultured overnight at 37° C. in a humidified 5% $CO_2$ atmosphere. 1 mg of particles was suspended in 0.1 mL of PBS and this was subsequently diluted 1:10 in serum free RPMI 1640 medium. Following removal of the original medium from each well, 100 μL of the particle suspension was placed in each well. Over a 3 h period this suspension was periodically removed and replaced with serum containing medium. A Xenogen IVIS® Lumina imaging system, equipped with an ICG filter set, was used to read the fluorescence signal and data were analysed using Living Image® software v.2.6. The data are presented in FIG. 2 and demonstrate that the ICG component of the nanoparticle affords an imaging capability that can be exploited to identify particle location.

Example 5—SDT Treatment Using RB+ICG Nanoparticles—In Vitro Studies

To demonstrate that the RB+ICG particles could elicit cytotoxic effects in vitro, three cell lines were employed as targets. BxPC3 cells are human pancreatic cancer cells, T110299 are mouse pancreatic cancer cells derived from a KPC genetically engineered mouse model carrying both Kras and p53 mutations, and hPSC cells are human pancreatic stellate cells. The latter serve as precursors of pancreatic fibroblasts and result in desmoplasia or the formation of fibrous connective tissues that form a pathological obstacle to effective treatment. While BxPC3 cells were cultured in RPMI 1640 medium supplemented with 10% fetal bovine serum and 1% penicillin/streptomycin, the T110299 cells were cultured in high glucose DMEM supplemented with 10% fetal bovine serum, 1% non-essential amino acids, 1% L-glutamine and 1% penicillin/streptomycin, and the hPSC line was cultured in high glucose DMEM supplemented with 10% fetal bovine serum and 1% penicillin/streptomycin. BxPC3 cells, T110299 cells and hPSC were plated into 96-well plates at concentrations of $5 \times 10^3$, $1.5 \times 10^3$ and $3 \times 10^3$ cells per well, respectively and cultured overnight at 37° C. in a humidified 5% $CO_2$ atmosphere. Spent medium was removed from the wells and replaced with fresh serum-containing medium and both the BxPC3 and T110299 were treated with concentrations of nanoparticles at 0, 0.1, 0.5, 1 and 5 μM with respect to RB. Cells were also treated with free RB at a concentration of 0.5 μM. The hPSC cell line was treated with nanoparticles at 0, 0.01, 0.05, 0.1 and 0.5 μM with respect to RB and these cells were also treated with free RB at a concentration of 0.5 μM for comparative purposes. Both BxPC3 and T110299 cells were incubated for 24 h after which the medium was replaced. The hPSC line was incubated for 4 h with particles and the medium was then replaced. The latter was done because if the cells were treated for 24 h with the nanoparticles, no cells remained viable following subsequent treatment with ultrasound. Cells were then treated with ultrasound by placing the individual wells in contact with the ultrasound transducer and contact was mediated by an ultrasound gel. Each well was treated with ultrasound for 30 s at a frequency of 1 MHZ, a power density of 3 W/cm² and a duty cycle of 50% at a pulse repetition of 100 Hz. Plates were incubated for a further 24 h and cell viability was determined using the MTT assay. Cell viability was expressed as a % of the untreated control for each cell line. The data are shown in FIGS. 3A, B and C and they demonstrate: (i) that all 3 cell lines exhibited reduced cell viability in the presence of ultrasound and nanoparticles; (ii) for all three cell lines little or no toxicity was exhibited by the particles in the absence of ultrasound; (iii) the ultrasound conditions employed in the treatments had little or no effect on cell viability; and (iv) for all three cell lines the reduction in viability obtained with ultrasound together with particles containing 0.5 μM RB exhibited a similar reduction in cell viability to cells treated with ultrasound and the free RB at that concentration. Surprisingly, it was found that the hPSC were more susceptible to SDT than the two cancer cell lines since a lower concentration of nanoparticles provided a greater reduction in cell viability. This could prove useful in the treatment of pancreatic cancer in particular, since specific eradication of such cells may have a negative impact on desmoplasia.

Example 6—SDT Treatment Using RB+ICG+IM Nanoparticles—In Vitro Studies

Figure 4:
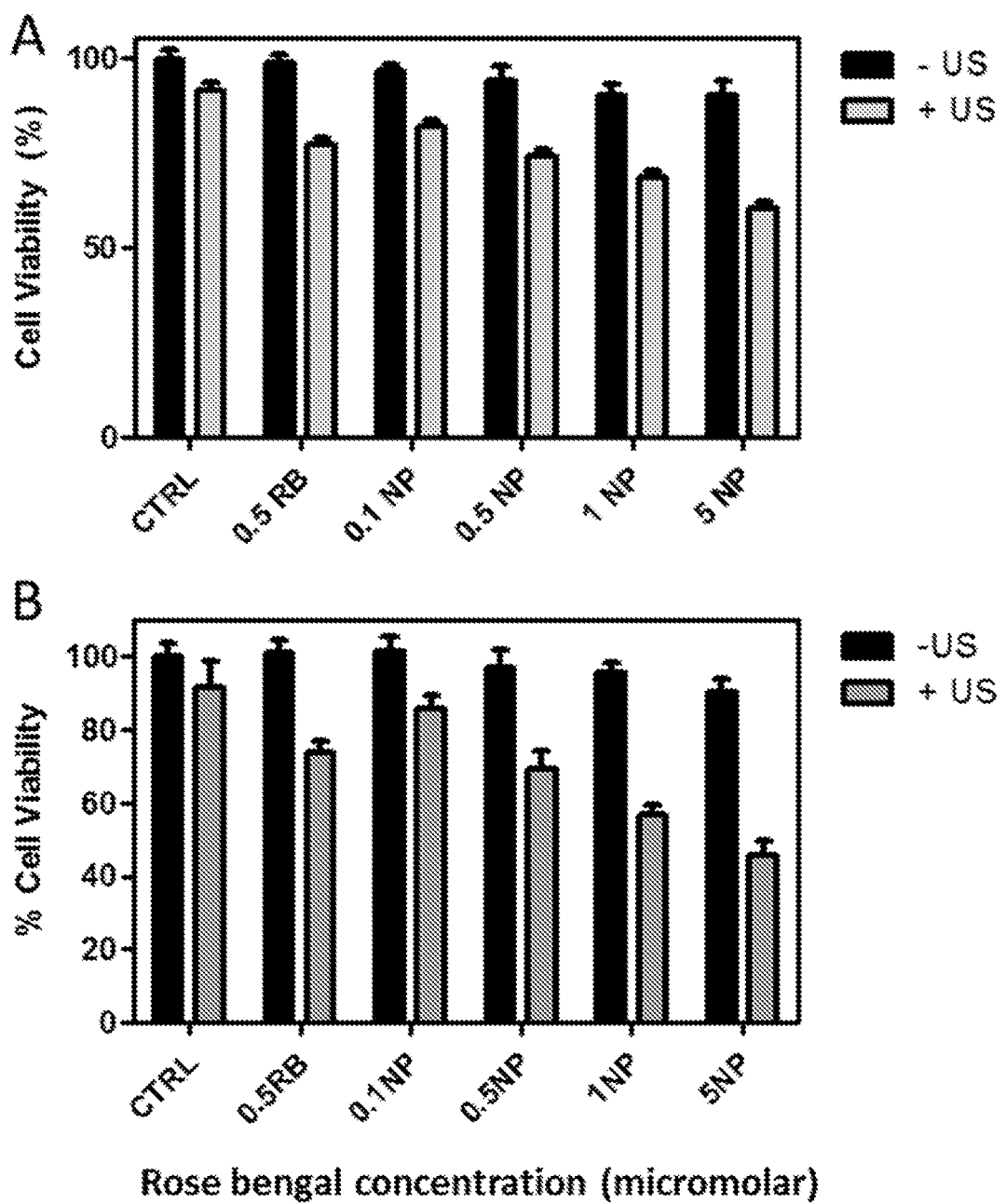
FIG. 4 shows the treatment of BxPC3 (A) and T110299 (B) with RB+ICG+IM nanoparticles in the presence (+US) and absence (−US) of ultrasound. Error bars represent ± SEM where n=6.

In order to confirm that the nanoparticles could still deliver an SDT effect following incorporation of IM into the particles, both BxPC3 and T110299 cells were treated with the RB+ICG+IM containing nanoparticles. Cells were prepared and treated as described in Example 5 and the results are shown in FIGS. 4A and 4B. The data confirm that inclusion of the IM does not have a negative impact on the ability of the nanoparticles to impart a cytotoxic effect in the presence of ultrasound.

Example 7—Distribution of RB+ICG Nanoparticles In Vivo

Figure 5:
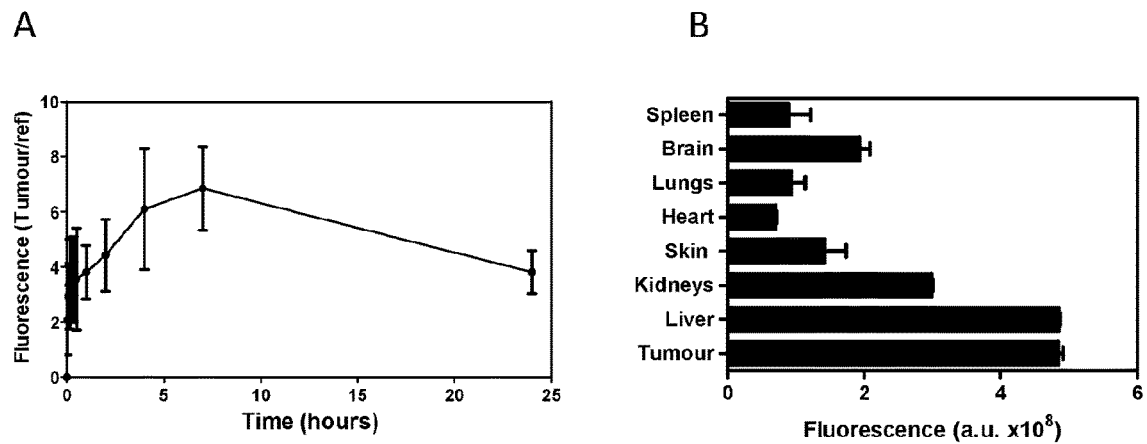
FIG. 5 shows whole body (A) (n=3) and excised organ (B) (n=2) nIR fluorescence imaging to demonstrate tumour sequestration of RB+ICG nanoparticles. For A the error bars represent ± SD.

In order to confirm that the incorporation of ICG into the nanoparticles provides an imaging capability and to further exploit this aspect to assess both tumour sequestration of the particles and organ distribution, a human pancreatic tumour xenograft model (BxPC3) was employed in SCID mice. All animals were treated humanely and in accordance with licensed protocols under the UK Animal (Scientific procedures) Act 1986. Tumours were generated by injecting $1 \times 10^6$ cells suspended in 100 μL of a 1:1 mixture of complete medium (RPMI 1640 supplemented with 10% fetal bovine serum and 1% penicillin/streptomycin) and Matrigel™ subcutaneously into the rear dorsum of 8 week old SCID mice. Once tumours had reached an average size of 110 mm³, animals were anaesthetised using Hypnorm/Hypnovel administered intraperitoneally and a 100 μL aliquot of nanoparticles suspended in PBS to ensure delivery of RB at a concentration of 250 μM, was then administered intravenously to each animal. Following administration of the nanoparticles, the anesthetised animals were imaged using nIR fluorescence imaging as described in Example 4. In analysing the data a reference point on an extremity of the animal was chosen as a surrogate of whole body fluorescence and the ratio of the signal obtained from the tumour region was expressed relative to that reference to semi-quantitatively determine selective uptake of nanoparticles by the tumour. The data are shown in FIG. 5A and they demonstrate that the signal in the tumour, relative to whole body fluorescence increased greater than 6-fold in the first 7 h and this subsequently decreased to 4-fold at 24 h. These data demonstrate that the nanoparticles were being sequestered in the tumour following administration. Preferential uptake by the tumour was confirmed by sacrificing the animals and surgically removing and imaging relevant organs. The data in FIG. 5B indicate that in relative terms a significant signal was obtained from both the tumour and the liver with both kidney and brain exhibiting the next highest signal. Although a similar signal was obtained for both the liver and the tumour using the nanoparticles, Yue et al. (May 2019 Nat Commun. 2019 May 2; 10 (1): 2025) using a liposomal formulation bearing a sensitizer and immune modulator as payloads, demonstrated that the liver contained over twice the amount of liposomes than the tumour at 24 h. In comparative terms the invention is superior to the liposomal formulation described in Yue et al. since it clearly demonstrates a greater degree of tumour sequestration of the polymeric nanoparticles. In overall terms the data confirm that incorporation of ICG into the nanoparticles provides an imaging capability and this has been exploited to demonstrate a higher degree of preferential tumour sequestration of the nanoparticles than previously demonstrated.

Example 8—SDT Treatment of Human Pancreatic Xenograft Tumours Using RB+ICG Nanoparticles To demonstrate that the RB+ICG nanoparticles could be employed for SDT, BxPC3 tumours were established in SCID mice as described for Example 7. When tumours had reached an average size of 110 $mm^3$, nanoparticles were administered intravenously to mice as described for Example 6. 30 min. after administration of nanoparticles, the relevant animals were treated with ultrasound for 3.5 min at a frequency of 1 MHZ, a power density of 3.5 $W/cm^2$ and a duty cycle of 30%, using a pulse repetition frequency of 100 Hz. Animals were treated with nanoparticles and ultrasound as indicated by the arrows in FIG. 6. Control animals either received nanoparticles alone at the times indicated by the arrows in FIG. 6 or were untreated. Tumour volume was monitored at the times indicated in FIG. 6. The data demonstrate that for animals treated with nanoparticles followed by ultrasound, tumour growth was dramatically reduced. These results demonstrate that these nanoparticles can elicit an SDT effect in vivo.

Example 9—Demonstration of an Abscopal Effect Using RB+ICG Nanoparticle-Mediated SDT In order to demonstrate that RB+ICG nanoparticle-induced SDT can elicit an abscopal effect, i.e. impart a therapeutic effect at an off-target tumour, two tumours were induced in each animal. For these studies the cell line, T110299 described above in Example 5, was used to generate tumours in 8 week old immunocompetent C57BL/6J mice. A tumour was established on each side of the rear dorsum of each mouse by subcutaneously injecting each site with a 100 μL aliquot containing $0.5 \times 10^6$ T110299 cells suspended in a 1:1 mixture of complete medium (DMEM supplemented as described in Example 5) and PBS. When tumours reached an average size of 130 $mm^3$ animals were treated. When treating with nanoparticles and with the exception of the time of treatment, these were administered intravenously as described for Example 8. When treating with ultrasound, with the exception of the days on which animals were treated, conditions were the same as those described in Example 8 and in all cases only the target tumour received ultrasound. Animal groups consisting of 5 animals each were (1) untreated, (2) treated with ultrasound alone, (3) treated with RB+ICG nanoparticles alone and (4) treated with RB+ICG nanoparticles together with ultrasound. The size of both the target and off-target tumours were monitored and the data obtained are shown in FIGS. 7A and B. As shown in FIG. 7A, the target tumours receiving the combined treatment with both nanoparticles and ultrasound exhibited a dramatic decrease in tumour growth, while nanoparticles or ultrasound had any impact on tumour growth. These data confirm those described in Example 8, demonstrating that the nanoparticles could be employed for SDT. In examining growth of the off-target tumour, i.e. the tumour that did not receive ultrasound treatment in each animal (FIG. 7B), again a dramatic decrease in tumour growth in animals receiving the combined treatment of nanoparticles plus ultrasound was observed and again, no difference in growth was observed in animals treated with nanoparticles or ultrasound alone. The data demonstrate that the RB+ICG nanoparticles can elicit a potent abscopal effect. In contrast, the liposomal formulation described by Yue et al., (2019) failed to elicit an abscopal effect in the absence of an immune checkpoint inhibitor using an ectopic model, even when their formulation contained the immune modulator imiquimod. Although they describe an abscopal effect in the absence of an immune checkpoint inhibitor using an orthotopic model, their effect is weaker than that observed at their primary target lesion. In overall terms the data obtained using the invention suggest that treatment of a single tumour with RB-ICG-mediated SDT could potentially be used to control disease at metastatic sites.

Example 10—Enhanced Abscopal Effect Using RB+ICG+IM Nanoparticle-Mediated SDT

Since an abscopal effect was detected using the RB+ICG nanoparticles, the immunomodulatory, imiquimod (IM), was then incorporated. This is a toll-like receptor agonist (TLR7) and it has been suggested that it and similar compounds (resiquimod, gardiquimod, 3M-011) can serve as immunomodulators capable of activating antigen presenting cells together with T and natural killer (NK) cells. Although TLR7 or TLR7/8 agonists have been used both in preclinical and clinical studies relating to the generation of protective immune responses in cancer, their utility in the treatment of pancreatic cancer is confusing with some reports suggesting a protective response and others even suggesting a potential cancer promoting response [Chi et al. (2017); Scholch et al. (2014); Zou et al. (2015); Ochi et al. (2012) and Grimmig et al. (2017)]. Therefore, in order to determine if IM would contribute any therapeutic advantage, this was incorporated into the nanoparticles as described in Example 1.

The target model employed in this study was the immunocompetent mouse model used in Example 9 and the comparative efficacy of particles containing RB+ICG and RB+ICG+IM was assessed, each in the presence and absence of ultrasound as indicated by arrows in FIG. 8 using the ultrasound treatment conditions described in Example 9. Particles were administered intravenously at the times indicated by arrows in FIG. 8 to relevant groups of tumour bearing animals at the concentration (with respect to RB) as described for Example 9 and tumour volume was monitored.

Control animals were untreated, treated with particles alone or treated with ultrasound alone. The data obtained are shown in FIG. 8 where A shows the effects of treatment on the ultrasound targeted tumour in each animal and B shows the effects on the tumour that did not receive ultrasound treatment. From the data in FIG. 8A, it can be seen that both the RB+ICG and the RB+ICG+IM particles deliver a similar response in terms of delivering a decrease in tumour growth. It was interesting to note also that the IM-containing particles did not exhibit any stimulatory effect on tumour growth in the group of animals that were treated with nanoparticles alone. However, at the off-target tumour (FIG. 8B) it was noted that the particles containing the IM resulted in a greater reduction in tumour growth, demonstrating that the inclusion of IM in the particles potentiated the therapeutic effect at the off-target tumour. These results demonstrate that the RB+ICG+IM nanoparticles could be used as a means of potentiating the effects of SDT, particularly for treating metastatic disease.

Example 11—the Protective Effect of RB+ICG+IM-Mediated SDT

Since it was shown that the abscopal effect delivered at the off-target tumour using RB-ICG+IM-mediated SDT was potentiated by inclusion of the IM in the particles, it was of interest to determine if this effect could protect animals from developing new tumours. If this was proven to be the case, it would suggest that the RB+ICG+IM-mediated SDT was capable of generating immunological memory by way of eliciting an adaptive immune response. To this end, the immunocompetent mouse pancreatic tumour model was again used as the target. In these studies a single tumour was established in each animal as described in Example 9. Animals were treated with RB+ICG- and RB+ICG+IM-mediated SDT as described for Example 10 and 24 h later, cells were injected into an off-target site on each animal in an attempt to establish a second tumour. The target tumour continued to be treated (nanoparticles and ultrasound) as indicated in FIG. 9. Growth of both the treated target tumour and any tumour that developed at the off-target site was monitored. The results are shown in FIG. 9, where A shows growth of target tumours and B shows growth of any tumours that established at the off-target site. The data clearly demonstrate that a decrease in tumour growth was observed in target tumours treated with RB+ICG- and RB+ICG+IM-mediated SDT, confirming previous results in Example 10. However, at the off-target site the only group that did not exhibit establishment of tumours was the group of animals treated with RB+ICG+IM-mediated SDT. In the study by Yue et al. (2019) all animals treated with their formulation in the absence of an immune checkpoint inhibitor developed tumours when rechallenged. With the invention, the results presented herein demonstrate that RB+ICG+IM-mediated SDT can provide a protective effect against the development of secondary lesions and confirms that it could play a role in control of metastatic disease. This result is surprising since it has previously been suggested that TLR7/8 agonists could play a developmental role in pancreatic cancer [Ochi et al. (2012) and Grimmig et al. (2017)].

Example 12—Impact of RB+ICG Nanoparticle-Mediated SDT on Tumour Stroma

Figure 3:
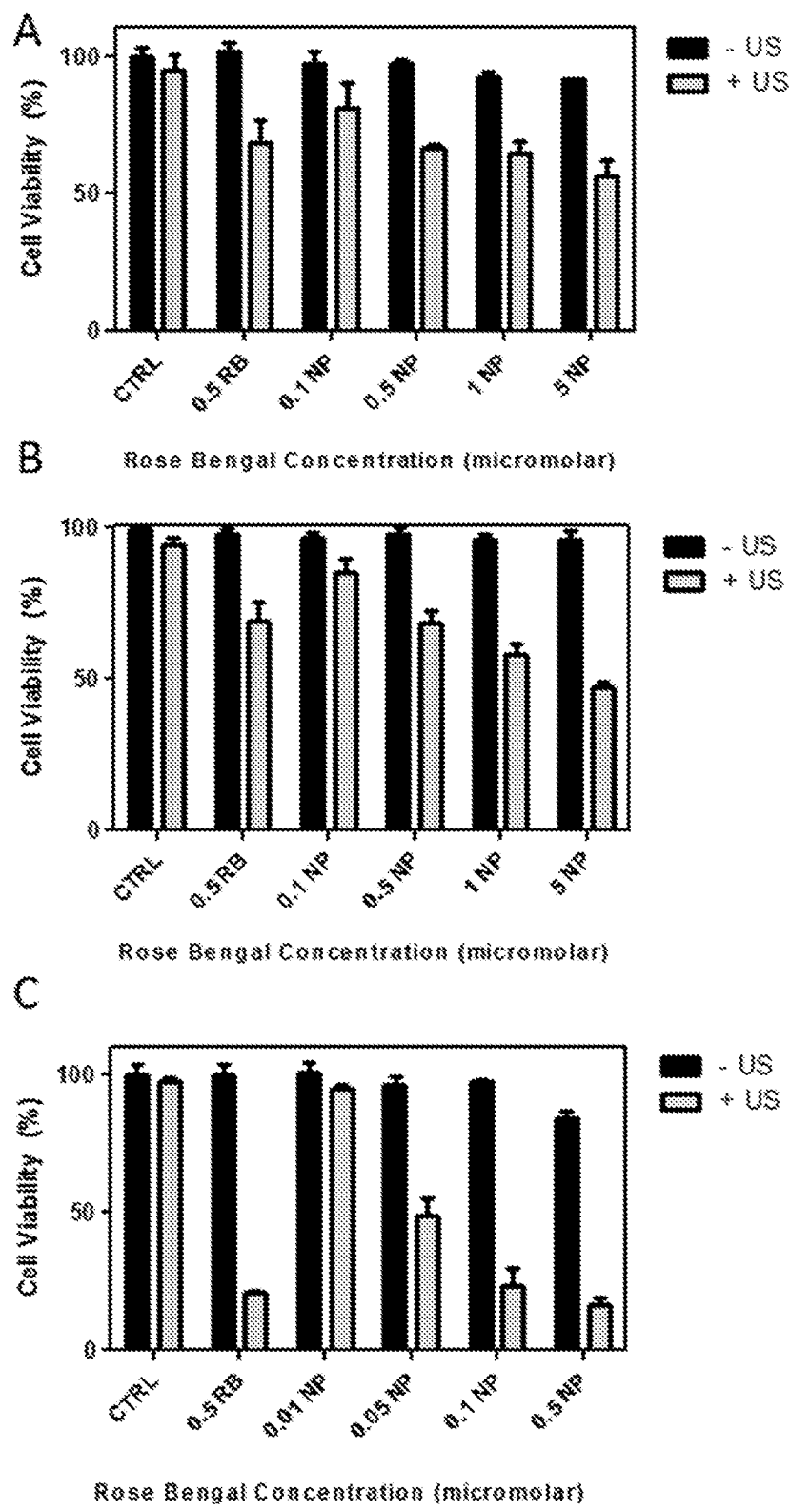
FIG. 3 shows the treatment of BxPC3 (A), T110299 (B) and hPSC (C) cells with RB+ICG nanoparticles in the presence (+US) and absence (−US) of ultrasound. Error bars represent ± SEM where n=5.

Since particle-mediated SDT exhibited a more potent effect with pancreatic stellate cells rather than cancer cells as demonstrated in Example 5 and FIG. 3, and since these cells serve as stromal precursors, it was decided to exploit histology together with specific stromal staining to examine residual tumour tissues in animals treated with particle-mediated SDT. Animals from the study described in Example 9 were sacrificed on day 11 and residual tumour tissues were surgically excised, fixed in 4% paraformaldehyde, embedded in paraffin and sectioned using a microtome into 5 µm sections prior to staining. The tumour sections were de-paraffinized in xylene and hydrated in graded ethanol prior to staining with haematoxylin for 3 minutes, followed by washing in warm tap water for 30 minutes and undergoing secondary staining with Picrosirius Red (Sirius Red stain for stroma) for 1 hour. After 2 quick washes in 0.5% acetic acid, ascending concentrations of ethanol were employed to dehydrate sections which were then cleared in two washes of xylene before mounting occurred with resinous mounting medium and glass coverslips. Images were captured using a Zeiss Microscope, and the percentage of Sirius Red positive pixels was quantified across all treatment groups using ImageJ (National Institutes of Health, USA).

The data obtained are shown in FIG. 10 and the stroma tissue is stained an intense red colour in all sections. However, direct observation of sections from tumours that were either untreated or treated with NPs alone demonstrated that the stroma is much more prevalent than in sections of residual tissue examined following treatment with NPs plus ultrasound. This was confirmed by quantitative comparison of red pixels (stroma) in all images using ImageJ as shown in FIG. 11. These results, taken together with the data from Example 5, demonstrate that NP-mediated SDT is capable of significantly modifying tumour stroma and this potentially offers a significant therapeutic benefit. It is well known that the existence of stroma in many solid tumours is a negative prognostic marker primarily because it promotes invasion and metastasis, and because it presents a barrier to entry of therapeutic drugs or cells of the immune system. It has been shown that drugs which disrupt the stromal barrier can be exploited to enable more effective drug- or immune-based therapies (Kianna et al., Cancer Research, 79:372-386, 2019). This example therefore demonstrates a clear and hitherto unforeseen advantage associated with NP-mediated SDT, particularly in the context of assisting immunotherapy. A SDT-induced decrease in tumour stroma would permit cells of the immune system to penetrate tumour tissues in order to be activated by either endogenously-generated antigens resulting from the SDT treatment (e.g. damage associated molecular patterns, DAMPs) and/or benefit from an exogenously added stimulant of the immune system simultaneously provided by the nanoparticles (e.g. imiquimod in the RB-ICG+IM nanoparticles).

Example 13—SDT-Mediated Enhanced Infiltration of Leukocytes and Cytotoxic T Cells into Tumours Following Treatment with RB+ICG or RB+ICG+IM Nanoparticles Since a dramatic abscopal effect was evident in particle-mediated SDT (as shown in FIGS. 7 and 8) it was decided to see if treatment of tumours resulted in infiltration of immune cells into those treated tumours. Animals bearing two tumours were established as described in Example 9 and were either untreated, treated with RB and ICG-containing nanoparticles plus ultrasound or treated with RB, ICG and imiquimod-containing nanoparticles plus ultrasound. As in Example 9, only one tumour in each animal (target) was exposed to ultrasound. Animals were sacrificed 48 h after treatment and both the target and off-target tumours were harvested from each animal. Tissues were homogenised in RPMI 1640 medium supplemented with 4% foetal bovine serum, 160 µL collagenase type II (30 mg/mL), 50 UL DNAse (2 µg/mL) and mixed gently for 15 min at room temperature. The suspension was filtered to remove clumps, washed with PBS by centrifugation at 150 g for 5 min and incubated with anti-CD45 (CD45+, leukocytes) and anti-CD8a (CD8a*, cytotoxic T cells) antibodies (Thermo Scientific, UK) for 30 min in the dark. Samples were washed twice with PBS by centrifugation and analysed using a Beckman Coulter Gallios flow cytometer (Beckman Coulter, UK) and post-acquisition analysis was completed using Kaluza analysis software (Beckman Coulter, UK).

The data obtained from these experiments are shown in FIGS. 12A and 12B. The data demonstrate no significant infiltration of leukocytes (CD45') into the untreated and RB+ICG nanoparticle-mediated SDT treated tumours, whereas a very dramatic and statistically significant (P<0.001) degree of infiltration of leukocytes occurred in the target tumour treated with the RB, ICG and imiquimod-containing nanoparticle-mediated SDT (FIG. 12A, Target; IMQ NP+US). Based on the effects of particle-mediated SDT on stroma (as shown in Example 11), one might have expected to find enhanced infiltration into SDT-treated target tumours for both the RB+ICG and RB+ICG+IMQ nanoparticle-mediated treatments (although it should be noted that SDT treatment might also be expected to catastrophically impact negatively on tumour vascularisation and this could preclude infiltration). Although undetectable infiltration of CD45' occurred in the target tumour treated with RB and ICG-containing nanoparticles plus ultrasound, it is apparent that a sufficient immune response is generated to provide a dramatic abscopal effect (FIGS. 7 and 8). In addition, although there is no statistically significant increase in infiltration of CD45' following treatment with each nanoparticle at the off-target tumours, there does appear to be an upwards trend observable (FIG. 12A, Off-target). This results from the generation of a tumour-specific immune response in the form of tumour homing immune cells that accumulate via the intact vasculature of the off-target tumour.

Incorporating imiquimod into the particles, enabling simultaneous delivery of both the sonosensitiser and the immunoadjuvant, results in a significant enhancement of tumour infiltrating leukocytes and this effect may be responsible for the enhanced abscopal effect observed in FIG. 8 at the off-target tumour following treatment with the imiquimod-containing particle. These suggestions are further supported by the data presented in FIG. 12B. This shows cytotoxic T cell (CD8a$^+$) infiltration and again similar patterns were observed at both the target and off-target tumours where a statistically significant (p<0.05) degree of infiltration was observed at the target tumours following treatment with the imiquimod-containing particles (IMQ NP+US) and an upward trend in cytotoxic T cell infiltration occurred in the off-target tumours when treated with each particle and subjected to ultrasound.

The data presented herein demonstrate a clear advantage associated with systemic co-delivery of the imiquimod together with the sonosensitiser in a single particle since (1) imiquimod is clinically incompatible with systemic administration; and (2) particle deposition at the target tumour enables co-placement of the sonosensitiser and immune stimulant at the target site, so that the latter is present during SDT-induced generation of DAMPs, thereby enabling a highly localised form of in situ vaccination.

The invention claimed is:

1. A method of sonodynamic therapy, said method comprising the step of administering to cells or tissues of a subject in need thereof a pharmaceutically effective amount of a particulate composition, and subjecting said cells or tissues to ultrasound irradiation,
    wherein the particulate composition comprises a plurality of polymeric particles,
    wherein the polymeric particles comprise a matrix of a biocompatible polymer and polyethyleneimine (PEI), wherein the content of PEI in the particle as a percentage of the biocompatible polymer is in the range from 1 to 10 wt. %, said matrix having incorporated therein an anionic or hydrophobic sonosensitiser, an immunomodulatory agent, and optionally an imaging agent, and
    wherein the sonosensitiser is selected from the group consisting of phenothiazine dyes, Rose Bengal, porphyrins, ATX-70, chlorins, benzochlorins, phthalocyanines, napthalocyanines, porphycenes, cyanines, azodipyromethines, acridine dyes, purpurins, pheophorbides, verdins, psoralens, hematoporphyrins, protoporphyrins, curcumins, and their pharmaceutically acceptable salts.

2. The method as claimed in claim 1 wherein the sonodynamic therapy is used for the treatment of cancer, metastasis or micrometastasis derived from said cancer, in the treatment of circulating tumour cells (CTCs), in the treatment of multiple primary tumours, or in the treatment of a deep-sited tumour, metastasis or micrometastasis derived from said tumour.

3. The method as claimed in claim 2 wherein the sonodynamic therapy is used for the treatment of pancreatic cancer or metastatic pancreatic cancer.

4. The method as claimed in claim 1 wherein the sonodynamic therapy is used for the reduction of secondary lesions in a subject.

5. The method as claimed in claim 1, wherein said polymeric particles are microparticles or nanoparticles.

6. The method as claimed in claim 1, wherein said matrix forms the body of the particles or wherein said matrix forms the shell of the particles.

7. The method as claimed in claim 1, wherein said biocompatible polymer is selected from the group consisting of poly(caprolactone) (PCL), poly(lactic acid) (PLA), poly (L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLLA), and any blend thereof.

8. The method as claimed in claim 1, wherein said biocompatible polymer is poly(lactic acid-co-glycolic acid) (PLGA).

9. The method as claimed in claim 8, wherein said biocompatible polymer has a weight average molecular weight ranging from 7,000 to 240,000 Da.

10. The method as claimed in claim 8, wherein said PLGA has a lactic acid:glycolic acid ratio of about 75:25.

11. The method as claimed in claim 1, wherein the PEI is branched, and/or wherein the PEI has a weight average molecular weight ranging from 500 to 100,000 Da.

12. The method as claimed in claim 1, wherein the content of PEI in the particle as a percentage of the biocompatible polymer is in the range from 1 to 5 wt. %.

13. The method as claimed in claim 1, wherein the sonosensitiser is Rose Bengal.

14. The method as claimed in claim 1, wherein said immunomodulatory agent is selected from the following and any pharmaceutically acceptable salts thereof: TLR7 agonists, CpG oligodeoxynucleotides, anti-galactosylceramide; immunoadjuvants; and low molecular weight immune checkpoint inhibitors.

15. The method as claimed in claim 14, wherein said immunomodulatory agent is imiquimod.

16. The method as claimed in claim 1, wherein the polymeric particles comprise an imaging agent.

17. The method as claimed in claim 16, wherein the imaging agent is a near-infra-red imaging agent, a radiocontrast agent, or an MR imaging agent.

18. The method as claimed in claim 17, wherein the near-infra-red imaging agent is indocyanine green.

19. A method of sonodynamic therapy which comprises at least the following steps:
(a) administering a particulate composition to affected cells or tissues of a subject in need thereof and subjecting said cells or tissues to ultrasound irradiation; and
(b) simultaneously, separately or sequentially administering to said subject a pharmaceutically effective amount of an immune checkpoint inhibitor,
wherein the particulate composition comprises a plurality of polymeric particles,
wherein the polymeric particles comprise a matrix of a biocompatible polymer and polyethyleneimine (PEI), wherein the content of PEI in the particle as a percentage of the biocompatible polymer is in the range from 1 to 10 wt. %, said matrix having incorporated therein an anionic or hydrophobic sonosensitiser, and optionally an immunomodulatory agent and/or an imaging agent, and
wherein the sonosensitiser is selected from the group consisting of phenothiazine dyes, Rose Bengal, porphyrins, ATX-70, chlorins, benzochlorins, phthalocyanines, napthalocyanines, porphycenes, cyanines, azodipyromethines, acridine dyes, purpurins, pheophorbides, verdins, psoralens, hematoporphyrins, protoporphyrins, curcumins, and their pharmaceutically acceptable salts.

\* \* \* \* \*